United States Patent
Homma et al.

(10) Patent No.: US 10,794,848 B2
(45) Date of Patent: Oct. 6, 2020

(54) GAS SENSOR INCLUDING FIRST ELECTRODE, SECOND ELECTRODE, METAL OXIDE LAYER, AND INSULATING FILM, AND FUEL-CELL VEHICLE INCLUDING THE GAS SENSOR

(71) Applicant: Panasonic Intellectual Property Management Co., Ltd., Osaka (JP)

(72) Inventors: Kazunari Homma, Kyoto (JP); Zhiqiang Wei, Osaka (JP)

(73) Assignee: PANASONIC SEMICONDUCTOR SOLUTIONS CO., LTD., Kyoto (JP)

( * ) Notice: Subject to any disclaimer, the term of this patent is extended or adjusted under 35 U.S.C. 154(b) by 352 days.

(21) Appl. No.: 15/416,000

(22) Filed: Jan. 26, 2017

(65) Prior Publication Data
US 2017/0131227 A1  May 11, 2017

Related U.S. Application Data

(63) Continuation of application No. PCT/JP2016/003178, filed on Jul. 4, 2016.

(30) Foreign Application Priority Data

Aug. 28, 2015  (JP) ................... 2015-169372

(51) Int. Cl.
*G01N 27/12* (2006.01)
*B60L 50/72* (2019.01)
(Continued)

(52) U.S. Cl.
CPC ......... *G01N 27/122* (2013.01); *B60K 15/063* (2013.01); *B60L 50/71* (2019.02);
(Continued)

(58) Field of Classification Search
CPC ... H01M 2250/00407; Y02T 90/30–38; B60K 15/063–07; B60K 2015/0321;
(Continued)

(56) References Cited

U.S. PATENT DOCUMENTS 5,362,975 A    11/1994  von Windheim et al.
5,543,025 A *  8/1996  Garzon .............. G01N 27/4071
                                                     204/415
(Continued)

FOREIGN PATENT DOCUMENTS

JP    59-058348   4/1984
JP    6-222027    8/1994
(Continued)

OTHER PUBLICATIONS

Pergament et al, Electrical Switching in Thin Film Structures Based on Molybdenum Oxides, Hindawi Publishing Corporation Journal of Experimental Physics vol. 2014, Article ID 951297, (Year: 2014).*

(Continued)

*Primary Examiner* — David L Singer
(74) *Attorney, Agent, or Firm* — McDermott Will & Emery LLP

(57) ABSTRACT

A gas sensor includes a first electrode having a first main surface and a second main surface opposite to the first main surface; a second electrode having a third main surface facing the second main surface and a fourth main surface opposite to the third main surface; a metal oxide layer disposed between the first electrode and the second electrode, and being in contact with the second main surface and the third main surface; and an insulating film covering at least a part of the first electrode, a part of the second electrode, and at least a part of the metal oxide layer. At least a part of the fourth main surface is exposed to gas which
(Continued)

contains a gas molecule including a hydrogen atom. A resistance value of the metal oxide layer decreases when the second electrode is in contact with the gas molecule.

13 Claims, 19 Drawing Sheets

(51) Int. Cl.
*H01M 8/0444* (2016.01)
*B60L 50/71* (2019.01)
*B60K 15/063* (2006.01)
*G01N 33/00* (2006.01)
*H01M 8/04664* (2016.01)
*H01M 8/04082* (2016.01)
*B60K 15/03* (2006.01)

(52) U.S. Cl.
CPC ............ *B60L 50/72* (2019.02); *G01N 27/128* (2013.01); *H01M 8/0444* (2013.01); *B60K 2015/0321* (2013.01); *B60K 2015/03315* (2013.01); *B60K 2015/0638* (2013.01); *G01N 27/125* (2013.01); *G01N 33/005* (2013.01); *G01N 33/0047* (2013.01); *H01M 8/04201* (2013.01); *H01M 8/04664* (2013.01); *H01M 2250/20* (2013.01); *Y02T 90/32* (2013.01)

(58) Field of Classification Search
CPC ........... B60K 2015/03315; B60L 58/30; B60L 50/70–72; G01N 33/005; G01N 33/0031; G01N 27/4074; G01N 27/4071; G01N 27/4141
USPC .......... 204/424, 426; 422/90; 73/31.06, 23.4
See application file for complete search history.

(56) References Cited

U.S. PATENT DOCUMENTS

| | | | | |
|---|---|---|---|---|
| 5,985,486 | A * | 11/1999 | Giron | G01N 27/4074 429/188 |
| 2002/0187075 | A1* | 12/2002 | Nadanami | G01N 27/4074 422/98 |
| 2003/0024813 | A1 | 2/2003 | Taniguchi | |
| 2003/0066763 | A1* | 4/2003 | Watanabe | G01N 33/005 205/792.5 |
| 2003/0089604 | A1* | 5/2003 | Nadanami | G01N 27/4074 204/424 |
| 2004/0261500 | A1* | 12/2004 | Ng | B82Y 15/00 73/31.05 |
| 2005/0228596 | A1* | 10/2005 | Shoji | G01N 27/18 702/24 |
| 2005/0229379 | A1* | 10/2005 | Totokawa | G01N 27/4071 29/592.1 |
| 2006/0049048 | A1* | 3/2006 | Kondo | G01N 27/4074 204/425 |
| 2006/0090541 | A1* | 5/2006 | Theil | G01N 27/122 73/23.34 |
| 2006/0169024 | A1* | 8/2006 | Shoji | B60H 1/008 73/23.2 |
| 2007/0209937 | A1* | 9/2007 | Hoagland | G01N 27/122 204/424 |
| 2013/0250658 | A1* | 9/2013 | Wei | H01L 45/08 365/148 |
| 2013/0277217 | A1* | 10/2013 | Zribi | G01N 27/4074 204/415 |
| 2014/0056056 | A1* | 2/2014 | Takagi | G11C 13/0007 365/148 |

FOREIGN PATENT DOCUMENTS

| | | |
|---|---|---|
| JP | 2003-166972 | 6/2003 |
| JP | 2003-240746 | 8/2003 |
| JP | 2003-272660 | 9/2003 |
| JP | 2004-061306 | 2/2004 |
| JP | 2007-278876 | 10/2007 |
| JP | 2013-068567 | 4/2013 |

OTHER PUBLICATIONS

Conder, Electronic and ionic conductivity in metal oxides, Laboratory for Developments and Methods, Paul Scherrer Institute (Year: 2012).*
Ielmini, Resistive switching memories based on metal oxides: mechanisms, reliability and scaling (Year: 2016).*
He et al, Memristive properties of hexagonal WO3 nanowires induced by oxygen vacancy migration, Nanoscale Research Letters 2013 (Year: 2013).*
Pergament et al, Electroforming and switching effects in yttrium oxide, phys. stat. sol. (a) 201, No. 7, 1543-1550 (2004) / DOI 10.1002/pssa.200306804 (Year: 2004).*
Shao et al, Recent progress in the phase-transition mechanism and modulation of vanadium dioxide materials, NPG Asia Materials (2018) 10: 581-605 (Year: 2018).*
Bondi et al, Electrical Conductivity in Oxygen-Deficient Phases of Transition Metal Oxides from First-Principles Calculations, Sandia National Laboratories (Year: 2013).*
Merriam-Webster Dictionary, definition: film (Year: 2014).*
Oxford Dictionary, definition: insulate (Year: 2019).*
Merriam-Webster Dictionary, definition: insulate (Year: 2014).*
Merriam-Webster Dictionary, definition Anode (Year: 2014).*
Merriam-Webster Dictionary, definition Cathode (Year: 2014).*
Merriam-Webster Dictionary, definition electrode (Year: 2013).*
WhatIs, What is diode? (Year: 2014).*
Techno Genius, Characteristics and Working of P-N Junction Diode (Year: 2014).*
National Programme on Technology Enhanced Learning, Webcourse Semiconductor Devices Module 2: PN Junction (II) (Year: 2015).*
ThomasNet, Thermionic and Semiconductor Diodes (Year: 2012).*
Eurocircuits, VIA-via hole (Year: 2015).*
The Extended European Search Report dated Oct. 5, 2018 for the related European Patent Application No. 16826277.2.
International Search Report of PCT application No. PCT/JP2016/003178 dated Aug. 23, 2016.
J.Yu et al., "Hydrogen gas sensing properties of Pt/Ta2O5 Schottky diodes based on Si and SiC substrates", Sensors and Actuators A 172, pp. 9-14, Dec. 2011.

* cited by examiner

Legends:
S501 - Former Introduction of Nitrogen
S502 - Introduction of Hydrogen
S503 - Latter Introduction of Nitrogen Legends:
832 - Gas sensor for Tank Chamber 830
852 - Gas sensor for Fuel Cell Chamber 850

GAS SENSOR INCLUDING FIRST ELECTRODE, SECOND ELECTRODE, METAL OXIDE LAYER, AND INSULATING FILM, AND FUEL-CELL VEHICLE INCLUDING THE GAS SENSOR

BACKGROUND

1. Technical Field

The present disclosure relates to a gas sensor for detecting a gas molecule including a hydrogen atom contained in gas and relates to a fuel-cell vehicle including the sensor.

2. Description of the Related Art

Recently, attempts for realizing hydrogen-based society have been being energetically performed in various fields. In particular, fuel-cell vehicles using hydrogen as the fuel are being expected as ultimate eco-cars and have also been placed on the market, and due to this marketing, infrastructure, such as hydrogen stations, have been steadily built. In such a circumstance, sensors for detecting hydrogen have been increasing their importance as those for securing the safety and security of hydrogen-based society.

For example, Japanese Unexamined Patent Application Publication No. 59-58348 discloses a gas sensor having an MIM structure formed by stacking a metal film, a gas-sensitive resistive film, and a metal film. In the gas sensor of Japanese Unexamined Patent Application Publication No. 59-58348, the gas-sensitive resistive film is an insulating film of tantalum pentoxide ($Ta_2O_5$) containing certain amounts of palladium (Pd) and glass and is disposed between upper and lower metal electrodes of platinum (Pt). In Japanese Unexamined Patent Application Publication No. 59-58348, it is described that the gas sensor can detect flammable gas containing hydrogen (hereinafter, referred to as hydrogen-containing gas).

In addition, for example, J. Yu, et al., Sensors and Actuators A, vol. 172 (2011), pp. 9-14 (hereinafter, referred to as Non Patent Literature 1) discloses a gas sensor having an MIS structure formed by stacking a metal, a gas-sensitive resistive film, and a semiconductor. The gas sensor of Non Patent Literature 1 is constituted of a layered product of Pt, $Ta_2O_5$, and silicon (Si) or silicon carbide (SiC) and detects gas containing hydrogen atoms. In Non Patent Literature 1, it is described that hydrogen-containing gas is detected based on a change in electric characteristics (for example, a change in I-V characteristics of the MIS structure) caused by reduction of $Ta_2O_5$ of the gas-sensitive resistive film by hydrogen atoms released from the hydrogen-containing gas due to the catalytic action of Pt.

In general, since the efficiency of releasing hydrogen atoms from hydrogen-containing gas by the catalytic action of Pt is increased with an increase in temperature, the detection sensitivity of a gas sensor is increased by heating. Accordingly, in both Japanese Unexamined Patent Application Publication No. 59-58348 and Non Patent Literature 1, a heater is disposed near the gas sensor and heats the gas sensor. For example, Japanese Unexamined Patent Application Publication No. 59-58348 describes heating of the gas sensor to 400° C., and Non Patent Literature 1 describes heating of the gas sensor to 100° C. to 150° C.

SUMMARY

In one aspect, the techniques disclosed here feature a gas sensor for detecting a gas molecule including a hydrogen atom contained in gas. The gas sensor in one aspect of the disclosure includes a first electrode having a first main surface and a second main surface opposite to the first main surface; a second electrode having a third main surface facing the second main surface of the first electrode and a fourth main surface opposite to the third main surface; a metal oxide layer disposed between the first electrode and the second electrode, and being in contact with the second main surface of the first electrode and the third main surface of the second electrode; and an insulating film covering at least a part of the first electrode, a part of the second electrode, and at least a part of the metal oxide layer. At least a part of the fourth main surface of the second electrode is not covered with the insulating film and is exposed to the gas. The metal oxide layer has characteristics of decreasing the resistance value of the metal oxide layer when the second electrode is in contact with the gas molecule.

These generic or specific aspects may be implemented with a system, a method, an integrated circuit, a computer program, or a recording medium or may be implemented by any combination of systems, apparatuses, methods, integrated circuits, computer programs, and recording media.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

Figure 1A:
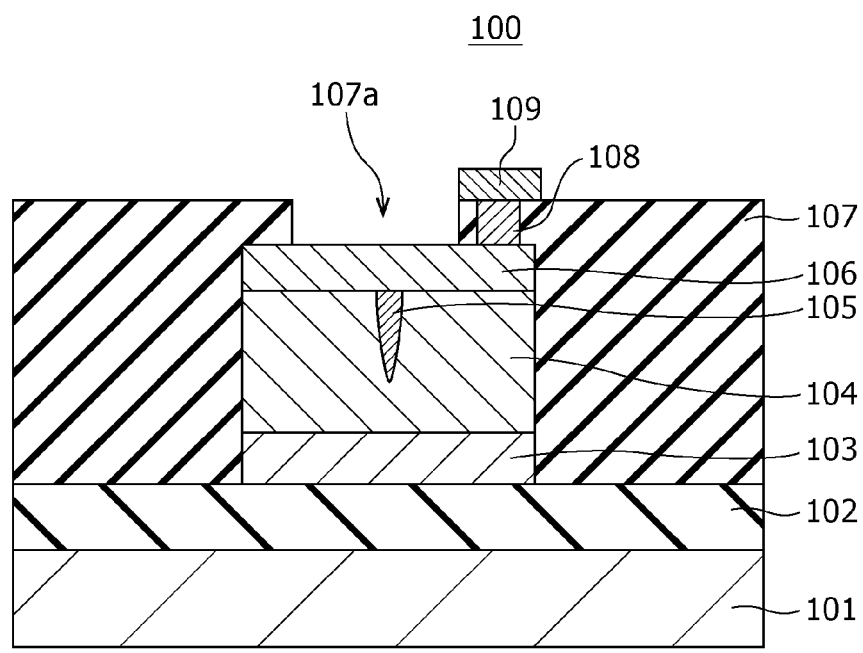
FIG. 1A is a cross-sectional view of a gas sensor according to First Embodiment.

DETAILED DESCRIPTION (Underlying Knowledge Forming Basis of the Present Disclosure)

The present inventors have diligently studied and, as a result, have found that known gas sensors have the following problems. In known gas sensors, elements for detecting gas are heated to 100° C. or more to improve the sensitivity in detection of hydrogen-containing gas, and the power consumption is about 100 mW at the lowest. Accordingly, if such a gas sensor is used in the ON-state at all times, a problem of increasing the power consumption is caused.

Accordingly, the present disclosure provides a gas sensor detecting hydrogen-containing gas with excellent power-saving properties.

(Aspects of the Present Disclosure)

A gas sensor according to an aspect of the present disclosure includes a first electrode having a first main surface and a second main surface opposite to the first main surface; a second electrode having a third main surface facing the second main surface of the first electrode and a fourth main surface opposite to the third main surface; a metal oxide layer disposed between the first electrode and the second electrode, and being in contact with the second main surface of the first electrode and the third main surface of the second electrode; and an insulating film covering at least a part of the first electrode, a part of the second electrode, and at least a part of the metal oxide layer. At least a part of the fourth main surface of the second electrode is not covered with the insulating film and is exposed to gas which contains a gas molecule including a hydrogen atom, and the metal oxide layer has characteristics of decreasing a resistance value of the metal oxide layer when the second electrode is in contact with the gas molecule.

In a gas sensor according to an aspect of the present disclosure, the metal oxide layer may include a local region being in contact with the second electrode, and a degree of oxygen deficiency of a metal oxide contained in the local region may be larger than a degree of oxygen deficiency of a metal oxide contained in the portion other than the local region in the metal oxide layer.

In a gas sensor according to an aspect of the present disclosure, the second electrode may contain a material having a catalytic action for releasing a hydrogen atom from the gas molecule including the hydrogen atom.

In a gas sensor according to an aspect of the present disclosure, the resistance value between the first electrode and the second electrode is decreased when gas containing a gas molecule including a hydrogen atom is in contact with the second electrode. This change in resistance value makes it possible to detect the presence of the gas molecule including a hydrogen atom in the gas as the object to be measured.

In such a configuration, the current flowing between the first electrode and the second electrode is concentrated in the local region containing the metal oxide having a high degree of oxygen deficiency. As a result, the temperature of the local region can be raised by a small quantity of current. This allows detection of hydrogen-containing gas by utilizing self-heating and gas sensitivity of the local region disposed inside the metal oxide layer, without heating with a heater, and gives a gas sensor having excellent power-saving properties.

The gas containing a gas molecule including a hydrogen atom is, for example, gas containing hydrogen, methane, or alcohol.

In a gas sensor according to an aspect of the present disclosure, the local region generates heat by the current flowing between the first electrode and the second electrode to release a hydrogen atom from the gas molecule at the portion of the second electrode being in contact with the local region. The released hydrogen atoms bind to oxygen atoms in the local region of the metal oxide layer to reduce the resistance value of the metal oxide layer.

In more detail, an increase in temperature of the local region also raises the temperature of the surface of the second electrode. The efficiency of releasing hydrogen atoms from the gas molecules including hydrogen atoms at the second electrode by the catalytic action of the second electrode is enhanced with an increase in temperature.

Hydrogen atoms are released from gas molecules including hydrogen atoms by bringing the gas molecules into contact with the second electrode, and the released hydrogen atoms diffuse in the second electrode and reach the local region. The hydrogen atoms then bind to oxygen of the metal oxide present in the local region to form water ($H_2O$), resulting in a further increase in the degree of oxygen deficiency of the local region. As a result, current easily flows in the local region, and the resistance between the first electrode and the second electrode is reduced.

If the gas molecules including hydrogen atoms disappear from the vicinity of the surface of the second electrode, water in the local region chemically reacts with the metal oxide being deficient in oxygen and is decomposed into hydrogen atoms and oxygen atoms. The hydrogen atoms diffuse in the second electrode, reach the surface of the second electrode, and become hydrogen molecules there to be discharged into the gas. At the same time, the oxygen atoms bind to the metal oxide being deficient in oxygen to reduce the degree of oxygen deficiency of the local region. As a result, current is difficult to flow in the local region to increase the resistance between the first electrode and the second electrode.

Thus, in a method of detecting hydrogen with a gas sensor that includes a first electrode and a second electrode disposed such that main surfaces face each other and includes a metal oxide layer disposed so as to be in contact with the main surface of the first electrode and the main surface of the second electrode, gas molecules including hydrogen atoms may be detected when the second electrode is in contact with gas containing the gas molecule including a hydrogen atom to reduce the resistance value between the first electrode and the second electrode. In such a method, since the metal oxide layer of the gas sensor generates heat only by the current flow for detecting the resistance value of the metal oxide layer, hydrogen-containing gas can be detected without heating with a separate heater.

Even if the local region is in a high resistance state or in a low resistance state, a further reduction in the resistance value is caused when hydrogen-containing gas is in contact with the second electrode. Accordingly, the gas sensor can detect the hydrogen-containing gas regardless of the state, a high resistance state or a low resistance state, of the local region.

Since the metal oxide layer of the gas sensor can reversibly transit between a high resistance state and a low resistance state showing a resistance value lower than that of the high resistance state, in order to further clearly detect a reduction in the resistance value of the metal oxide layer, the metal oxide layer of the gas sensor may be set to the high resistance state, and the second electrode may be brought into contact with gas.

In a gas sensor according to an aspect of the present disclosure, the metal oxide layer may be a layer having a property of reversibly transiting between a high resistance state and a low resistance state showing a lower resistance value than the high resistance state based on a voltage applied between the first electrode and the second electrode. In such a case, the local region can be electrically set to the high resistance state.

In a gas sensor according to an aspect of the present disclosure, the metal oxide layer may include a first metal oxide layer containing a first metal oxide and a second metal oxide layer containing a second metal oxide having a degree of oxygen deficiency smaller than a degree of oxygen deficiency of the first metal oxide; the first metal oxide layer may be in contact with the first electrode; the second metal oxide layer may be in contact with the second electrode; the local region may pass through at least the second metal oxide layer; and a degree of oxygen deficiency of the metal oxide contained in the local region may be larger than a degree of oxygen deficiency of the second metal oxide.

In a gas sensor according to an aspect of the present disclosure, the second electrode may contain at least one selected from the group consisting of platinum, palladium, and an alloy of platinum and palladium.

In a gas sensor according to an aspect of the present disclosure, the first metal oxide and the second metal oxide may be each independently a transition metal oxide or aluminum oxide.

In a gas sensor according to an aspect of the present disclosure, the transition metal oxide may be one selected from the group consisting of tantalum oxide, hafnium oxide, and zirconium oxide.

A gas sensor according to an aspect of the present disclosure may further include a via passing through the insulating film in a portion covering the part of the second electrode and connected to the second electrode, and a conductor connected to the via.

In a gas sensor according to an aspect of the present disclosure, the via may be disposed at a position not directly above the first electrode.

In such a configuration, the gas sensor can have excellent resistance change characteristics and high reliability by employing suitable structures and materials.

In a gas sensor according to an aspect of the present disclosure, the area of the metal oxide layer being in contact with the second main surface of the first electrode may be smaller than the area of the metal oxide layer being in contact with the third main surface of the second electrode.

In such a configuration, the outline of the first electrode viewed from the top can be disposed in a desired position within the second electrode. The local region is easily formed on the outline of the first electrode and therefore can be formed according to the position of the outline of the first electrode while avoiding the position having a risk of deteriorating the response time, for example, the position directly under the upper structures such as the via for connection. This can provide a gas sensor having excellent responsiveness.

A gas sensor according to an aspect of the present disclosure may further include a measurement circuit that, in operation, measures current flowing in the metal oxide layer when a voltage is applied between the first electrode and the second electrode.

A gas sensor according to an aspect of the present disclosure may further include a power supply circuit that, in operation, applies a voltage between the first electrode and the second electrode. In a gas sensor according to an aspect of the present disclosure, the power supply circuit may be configured so as to constantly apply a voltage between first electrode and the second electrode.

Such a configuration can provide a gas sensor having high convenience as a modular component including a measurement circuit or a power supply circuit.

A fuel-cell vehicle according to an aspect of the present disclosure includes a passenger compartment, a gas tank chamber accommodating a hydrogen gas tank, a fuel cell chamber accommodating a fuel cell, and a gas sensor according to an aspect of the present disclosure. The gas sensor is disposed in at least one selected from the group consisting of the gas tank chamber and the fuel cell chamber.

In a fuel-cell vehicle according to an aspect of the present disclosure, the gas sensor may be used for detecting hydrogen in the passenger compartment of the fuel-cell vehicle.

In a fuel-cell vehicle according to an aspect of the present disclosure, a voltage may be constantly applied to the gas sensor for judging whether hydrogen atoms are present in at least one of the outside of the hydrogen gas tank accommodated in the gas tank chamber and the outside of the fuel cell accommodated in the fuel cell chamber, based on the quantity of current flowing in the gas sensor.

Such a configuration can constantly monitor fuel gas leakage without significantly increasing the stand-by power of the fuel-cell vehicle by utilizing the excellent power-saving properties of the gas sensor. For example, since the presence or absence of fuel gas leakage has been already judged at the time of operating the ignition key, the start-up of the fuel-cell vehicle can be shortened, compared with the case of operating the gas sensor for judging the presence or absence of fuel gas leakage after operation of the ignition key. In addition, the safety can be improved by continuously monitoring fuel gas leakage after running the fuel-cell vehicle, for example, even after the fuel-cell vehicle has been housed in a garage.

In the present disclosure, the whole or a part of a unit, an apparatus, a member, or a part or the whole or a part of a functional block of a block diagram may be implemented by one or more electronic circuits including semiconductor apparatuses, semiconductor integrated circuits (ICs), or large scale integrations (LSTs). The LSIs or ICs may be integrated into one chip or may be constituted by combining a plurality of chips. For example, functional blocks other than recording elements may be integrated into one chip. Herein, those called LSI or IC change the names depending on the degree of integration, and those called system LSI, very large scale integration (VLSI), or ultra large scale integration (ULSI) may be used. In addition, a field programmable gate array (FPGA), which is programmed after production of an LSI, or a reconfigurable logic device, which can reconstitute the junction relationship inside an LSI or setting up the circuit section inside an LSI, can also be used for the same purpose.

Furthermore, the function or operation of the whole or a part of a unit, an apparatus, a member, or a part can be implemented by software treatment. In such a case, when the software is recorded in one or more non-temporary recording media, such as ROM, optical disk, or hard disk drive, and is implemented with a processor, the function specified by the software is implemented by a processor and peripheral devices. The system or apparatus may include one or more non-temporary recording media containing software, a processor, and a needed hardware device, such as an interface.

Embodiments of the present disclosure will now be described with reference to the drawings.

In the drawings, elements having substantially the same configurations, behaviors, and effects are denoted by the same reference symbols, and duplicate explanations are omitted. The numerical values, materials, methods of forming films, and other factors described below are all examples for specifically describing embodiments of the present disclosure, and the present disclosure is not limited to these examples. The connection relationships between components described below are examples for specifically describing embodiments of the present disclosure, and the connection relationships for putting the functions of the present disclosure into practice are not limited to these examples. Among the components in the following embodiments, the components not described in independent claims showing the highest-order concept will be described as arbitrary components.

(First Embodiment)
[Configuration of Gas Sensor]

The gas sensor according to First Embodiment has a metal-insulating film-metal (MIM) structure formed by stacking a gas-sensitive resistive film serving as a metal oxide layer and metal films. The gas sensor can detect hydrogen-containing gas, without heating with a heater, by utilizing self-heating and gas sensitivity of a local region formed in the gas-sensitive resistive film. Herein, the term "hydrogen-containing gas" is a generic name for gas composed of molecules including hydrogen atoms, and examples of the hydrogen-containing gas include hydrogen, methane, and alcohol.

FIG. 1A is a cross-sectional view illustrating an exemplary configuration of a gas sensor 100 according to First Embodiment.

Figure 1B:
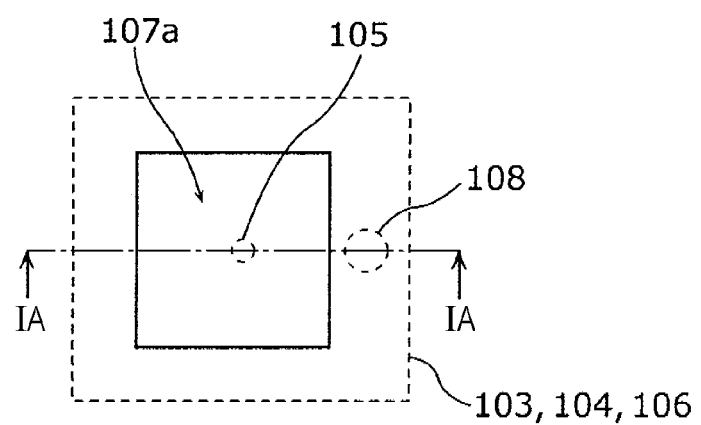
FIG. 1B is a top view of the gas sensor according to First Embodiment.

FIG. 1B is a top view illustrating an exemplary configuration of the gas sensor 100 according to First Embodiment. The cross section shown in FIG. 1A is that viewed from the direction indicated by the arrows on the cutting-plane line IA-IA of FIG. 1B.

The gas sensor 100 includes a substrate 101; an insulating film 102 disposed on the substrate 101; and a first electrode 103, a second electrode 106, a gas-sensitive resistive film 104 disposed between the first electrode 103 and the second electrode 106, an interlayer insulating film 107, a via 108, and a wiring conductor 109 disposed above the insulating film 102. In the first electrode 103, the lower surface is a first main surface, and the upper surface is a second main surface. In the second electrode 106, the lower surface is a third main surface, and the upper surface is a fourth main surface. The first electrode 103 and the second electrode 106 are disposed such that the second main surface faces the third main surface. The gas-sensitive resistive film 104 is disposed so as to be in contact with the second main surface of the first electrode 103 and the third main surface of the second electrode 106.

The interlayer insulating film 107 is provided with an opening 107a for bringing the second electrode 106 into contact with the gas as an object to be tested. In other words, while the interlayer insulating film 107 covers the first electrode 103, a part of the second electrode 106, and the gas-sensitive resistive film 104, at least a part of the fourth main surface, i.e., the upper surface, of the second electrode 106 is not covered by the interlayer insulating film 107 and is exposed to the gas as an object to be tested. In this embodiment, although the interlayer insulating film 107 covers the whole of the first electrode 103 and the whole of the gas-sensitive resistive film 104, the present disclosure is not limited to this configuration. The interlayer insulating film 107 may partially cover the first electrode 103 and the gas-sensitive resistive film 104.

The gas-sensitive resistive film 104 is disposed between the first electrode 103 and the second electrode 106. The gas-sensitive resistive film 104 is a layer reversibly changing the resistance value based on the electrical signal provided between the first electrode 103 and the second electrode 106. For example, the gas-sensitive resistive film 104 reversibly transits between a high resistance state and a low resistance state based on the voltage provided between the first electrode 103 and the second electrode 106 and the presence or absence of hydrogen-containing gas in the gas coming into contact with the second electrode 106.

Herein, the inside of the gas-sensitive resistive film 104 contains a local region 105 being in contact with the second electrode 106 and not being in contact with the first electrode 103. The metal oxide contained in the local region 105 has a degree of oxygen deficiency larger than that of the metal oxide contained in the portion other than the local region 105 in the gas-sensitive resistive film 104. The degree of oxygen deficiency of the metal oxide contained in the local region 105 reversibly changes based on the application of an electrical signal provided between the first electrode 103 and the second electrode 106 and the presence or absence of hydrogen-containing gas in the gas coming into contact with the second electrode 106. The local region 105 is a minute region containing a filament consisting of an oxygen defect site. The filament functions as a conductive path.

The interlayer insulating film 107 is provided with a via 108 in the portion covering the second electrode 106. The via 108 passes through the interlayer insulating film 107 and reaches the second electrode 106. A wiring conductor 109 is disposed on the via 108.

In the present specification, the term "degree of oxygen deficiency" refers to the ratio of the amount of deficient oxygen to the amount of oxygen contained in the oxide having the stoichiometric composition of a metal oxide. Herein, if a metal oxide has multiple stoichiometric compositions, in the present specification, the stoichiometric composition of the metal oxide is that having the highest resistance value. A metal oxide is more stable and has a higher resistance value at the stoichiometric composition compared with that at another composition.

For example, when the metal is tantalum (Ta), the oxide having the stoichiometric composition according to the above-described definition is $Ta_2O_5$. $Ta_2O_5$ can also be expressed as $TaO_{2.5}$. The degree of oxygen deficiency of $TaO_{2.5}$ is 0%. In $TaO_{1.5}$, the degree of oxygen deficiency is (2.5−1.5)/2.5=40%. In a metal oxide in an oxygen-excess state, the degree of oxygen deficiency is a negative value. In the present specification, the degree of oxygen deficiency is any of a positive value, 0, and a negative value, unless otherwise specified.

A metal oxide having a low degree of oxygen deficiency has a composition close to that of the metal oxide having the stoichiometric composition and therefore has a high resistance value, whereas a metal oxide having a high degree of oxygen deficiency has a composition close to that of the metal constituting the metal oxide and therefore has a low resistance value.

The term "oxygen content" refers to the ratio of the number of oxygen atoms to the total number of atoms. For example, the oxygen content of $Ta_2O_5$ is the ratio of the number of oxygen atoms to the total number of atoms (O/(Ta+O)) and is 71.4 atm %. Accordingly, the oxygen content of tantalum oxide in an oxygen deficiency state is larger than 0 and smaller than 71.4 atm %.

The local region 105 is formed inside the gas-sensitive resistive film 104 by applying an initial break voltage between the first electrode 103 and the second electrode 106. Herein, the initial break voltage may be a voltage having an absolute value larger than that of the ordinary write-in voltage that is applied between the first electrode 103 and the second electrode 106 for reversibly transiting the gas-sensitive resistive film 104 between a high resistance state and a low resistance state. Alternatively, the initial break voltage may be a voltage having an absolute value smaller than that of the write-in voltage. In this case, the initial break voltage may be repeatedly applied or may be continuously applied for a predetermined period of time. As shown in FIG. 1A, the application of the initial break voltage forms a local region 105 in the gas-sensitive resistive film 104 so as to be in contact with the second electrode 106 and not to be in contact with the first electrode 103.

The local region 105 is conceived to contain a filament consisting of an oxygen defect site. The local region 105 has a minute size matching with the filament necessary for applying electrical current. The formation of the filament in the local region 105 will be described using a percolation model.

The percolation model is based on a theory that the probability of forming a connection of oxygen defect sites (hereinafter, simply referred to as defect sites) is increased when the density of the defect sites exceeds a certain threshold in a hypothetical random distribution of the defect sites in the local region 105.

In the percolation model, a filament is constituted of a plurality of defect sites being connected to one another in the local region 105. In addition, in the percolation model, the change in resistance of the gas-sensitive resistive film 104 is caused through generation and dissipation of defect sites in the local region 105.

Herein, the term "defect" means that oxygen in a metal oxide is deficient compared with that at the stoichiometric composition. The term "density of defect sites" corresponds to a degree of oxygen deficiency. That is, the density of defect sites increases with the degree of oxygen deficiency.

The local region 105 may be formed at only one part of the gas-sensitive resistive film 104 of a gas sensor 100. The number of local regions 105 in the gas-sensitive resistive film 104 can be determined by, for example, electron beam absorbed current (EBAC) analysis.

The formation of the local region 105 in the gas-sensitive resistive film 104 allows the current in the gas-sensitive resistive film 104 to concentratedly flow in the local region 105 when a voltage is applied between the first electrode 103 and the second electrode 106.

Since the size of the local region 105 is very small, the temperature thereof is notably raised by, for example, heat generation due to a current of about several tens microamperes (i.e., a power consumption of less than 0.1 mW) at the time of application of a voltage of about 1 V for reading out the resistance value.

Accordingly, the efficiency of releasing hydrogen atoms from hydrogen-containing gas is increased by forming the second electrode 106 by a metal having a catalytic action, such as Pt, and heating the second electrode 106 in the portion being in contact with the local region 105 by the heat generated in the local region 105.

As a result, if the gas as an object to be tested contains hydrogen-containing gas, the hydrogen atoms released from the hydrogen-containing gas at the second electrode 106 bind to oxygen atoms in the local region 105 to reduce the resistance value of the local region 105.

The gas sensor 100 thus has characteristics of decreasing the resistance value of the gas-sensitive resistive film 104 by bringing the second electrode 106 into contact with hydrogen-containing gas. Such characteristics allow the detection of hydrogen-containing gas contained in the gas as an object to be tested by bringing the gas into contact with the second electrode 106 and thereby decreasing the resistance value between the first electrode 103 and the second electrode 106.

Furthermore, even if the local region 105 is in any of the high resistance state and the low resistance state, a further reduction in resistance value is caused by bringing hydrogen-containing gas into contact with the second electrode 106. Accordingly, the hydrogen-containing gas can be detected with a gas sensor 100 having the local region 105 being in any of the high resistance state and the low resistance state. However, in order to more clearly detect a reduction in resistance value, the gas sensor 100 may be used by electrically setting the local region 105 to a high resistance state.

The details for obtaining a gas sensor 100 having stable resistance change characteristics will now be described.

The gas-sensitive resistive film 104 contains a metal oxide in an oxygen deficiency state. The mother metal of the metal oxide may be at least one selected from the group consisting of transition metals, such as tantalum (Ta), hafnium (Hf), titanium (Ti), zirconium (Zr), niobium (Nb), tungsten (W), nickel (Ni), and iron (Fe); and aluminum (Al). Since transition metals have multiple oxidation states, different resistance states can be achieved by a redox reaction.

Herein, the term "metal oxide in an oxygen deficiency state" refers to a metal oxide that is usually an insulating material and has an oxygen content (atomic ratio) lower than that of the composition of a metal oxide having a stoichiometric composition. Many of metal oxides in oxygen deficiency states usually behave like semiconductors. A gas sensor 100 can achieve high reproducibility and stable resistance change behavior by using a metal oxide in an oxygen deficiency state in the gas-sensitive resistive film 104.

For example, when the gas-sensitive resistive film 104 contains hafnium oxide as the metal oxide, the resistance value of the gas-sensitive resistive film 104 can be stably changed by adjusting the value of x of $HfO_x$ representing the composition to 1.6 or more. In such a case, the hafnium oxide film may have a thickness of 3 to 4 nm.

When the gas-sensitive resistive film 104 contains zirconium oxide as the metal oxide, the resistance value of the gas-sensitive resistive film 104 can be stably changed by adjusting the value of x of $ZrO_x$ representing the composition to 1.4 or more. In such a case, the zirconium oxide film may have a thickness of 1 to 5 nm.

When the gas-sensitive resistive film 104 contains tantalum oxide as the metal oxide, the resistance value of the gas-sensitive resistive film 104 can be stably changed by adjusting the value of x of $TaO_x$ representing the composition to be 2.1 or more.

The compositions of the above-mentioned metal oxide layers can be measured by Rutherford backscattering spectrometry.

The materials for the first electrode 103 and the second electrode 106 are selected from, for example, platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), and titanium aluminum nitride (TiAlN).

Specifically, as the material for the second electrode 106, a material having a catalytic action of releasing hydrogen atoms from gas molecules including hydrogen atoms, such as platinum (Pt), iridium (Ir), and palladium (Pd), is used. As the material for the first electrode 103, a material having a standard electrode potential lower than that of the metal constituting the metal oxide, such as tungsten (W), nickel (Ni), tantalum (Ta), titanium (Ti), aluminum (Al), tantalum nitride (TaN), and titanium nitride (TiN), may be used. The standard electrode potential has characteristics that oxidation becomes difficult with an increase in the value.

The substrate 101 can be, for example, a silicon single crystal substrate or a semiconductor substrate, but is not limited to these substrates. Since the gas-sensitive resistive film 104 can be formed at a relatively low substrate temperature, for example, the gas-sensitive resistive film 104 can also be formed on a material such as a resin material.

The gas sensor 100 may further include a load element electrically connected to the gas-sensitive resistive film 104, such as a fixed resistance, a transistor, or a diode.

Furthermore, the gas sensor 100 may include a measurement circuit for measuring the current flowing in the gas-sensitive resistive film 104 when a certain voltage is applied between the first electrode 103 and the second electrode 106. The gas sensor 100 may include a power supply circuit for constantly applying a certain voltage between the first electrode 103 and the second electrode 106. Such a configuration can provide a gas sensor having high convenience as a modular component including a measurement circuit or a power supply circuit.

[Method of Producing Gas Sensor and Behavior]

An example of a method of producing the gas sensor 100 will then be described with reference to FIGS. 2A to 2G.

Figure 2A:
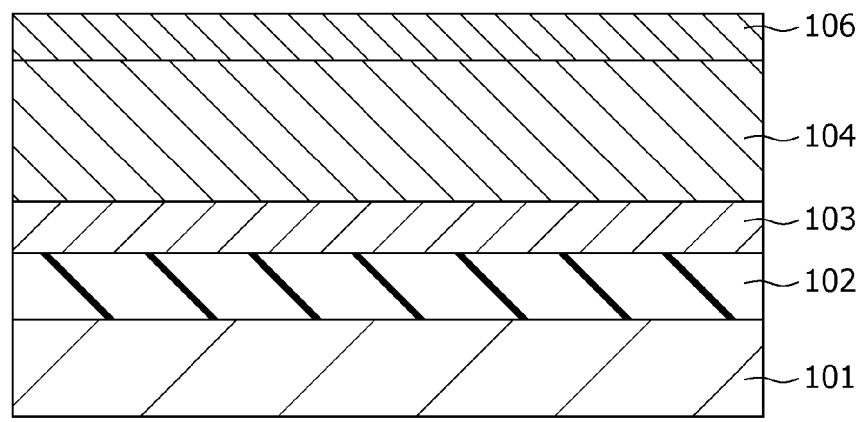
FIG. 2A is a cross-sectional view illustrating a method of producing the gas sensor according to First Embodiment.

First, as shown in FIG. 2A, an insulating film 102 having a thickness of 200 nm is formed on a substrate 101, for example, of single crystal silicon by a thermal oxidation method. Subsequently, a first electrode 103 of, for example, a Pt film having a thickness of 100 nm is formed on the insulating film 102 by sputtering. In addition, an adhesion layer of, for example, Ti or TiN may be formed between the first electrode 103 and the insulating film 102 by sputtering. Then, a metal oxide layer in an oxygen deficiency state, which is formed into a gas-sensitive resistive film 104, is formed on the first electrode 103 by reactive sputtering using, for example, a Ta target. A gas-sensitive resistive film 104 is thus formed.

Herein, regarding the thickness of the gas-sensitive resistive film 104, a too large thickness causes disadvantages of, for example, giving a too high initial resistance value, and a too small thickness causes a disadvantage of not providing a stable resistance change. For these reasons, the thickness may be about 1 nm or more and about 8 nm or less.

Subsequently, a second electrode 106 of, for example, a Pt film having a thickness of 150 nm is formed on the gas-sensitive resistive film 104 by sputtering.

Figure 2B:
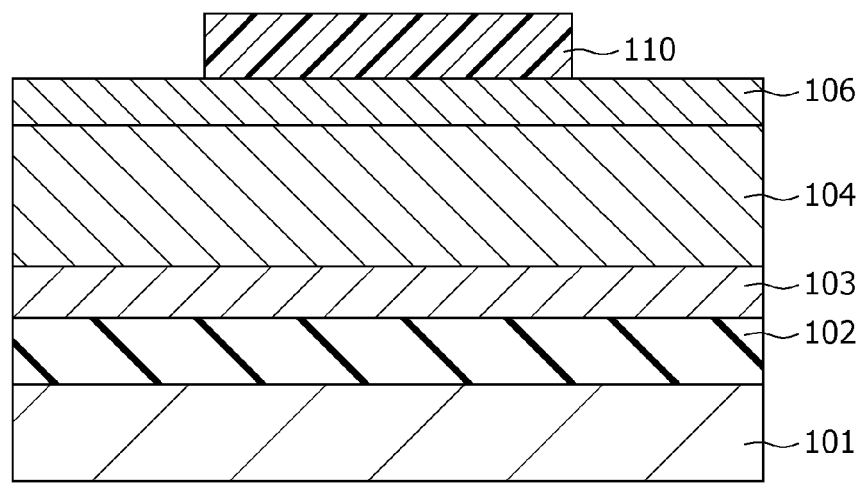
FIG. 2B is a cross-sectional view illustrating the method of producing the gas sensor according to First Embodiment.
Figure 2C:
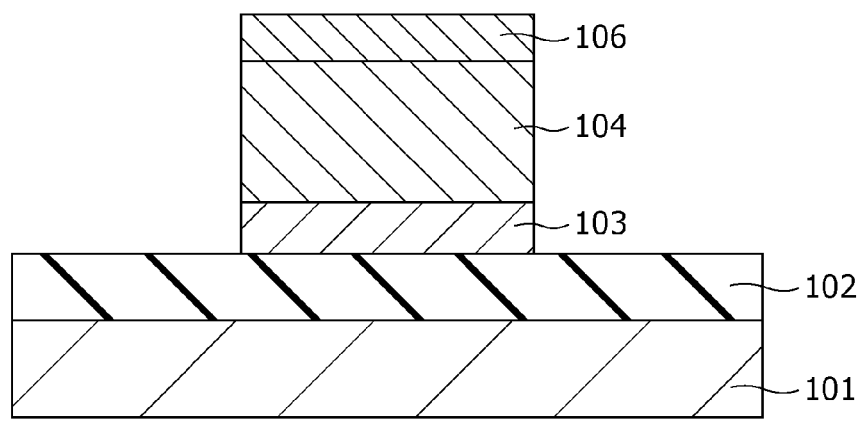
FIG. 2C is a cross-sectional view illustrating the method of producing the gas sensor according to First Embodiment.

Subsequently, as shown in FIG. 2B, a photoresist mask 110 is formed by a photolithography process. Then, as shown in FIG. 2C, the first electrode 103, the gas-sensitive resistive film 104, and the second electrode 106 are formed into the shape of an element by dry etching using the mask 110.

Figure 2D:
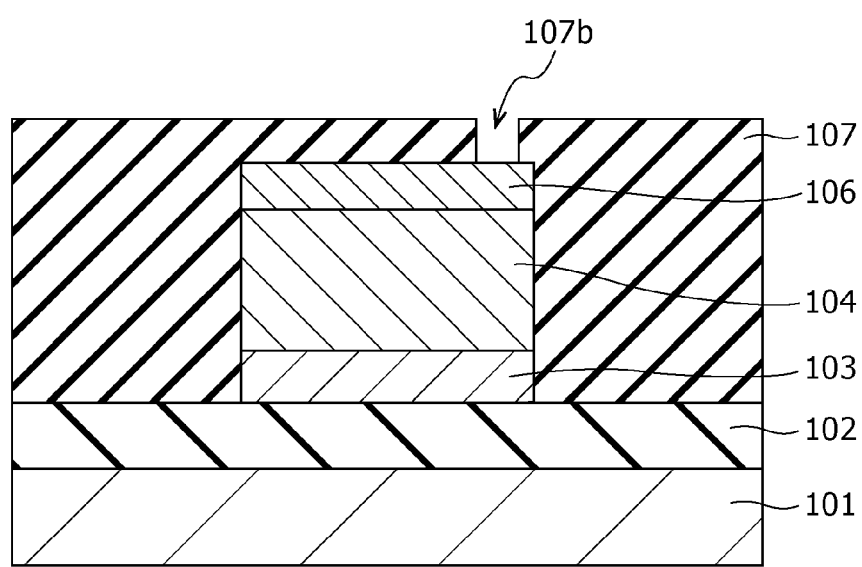
FIG. 2D is a cross-sectional view illustrating the method of producing the gas sensor according to First Embodiment.

Then, as shown in FIG. 2D, an interlayer insulating film 107 is formed so as to cover the insulating film 102, the first electrode 103, the gas-sensitive resistive film 104, and the second electrode 106. A via hole 107b reaching a part of the upper surface of the second electrode 106 is then formed in the interlayer insulating film 107 by etching.

Figure 2E:
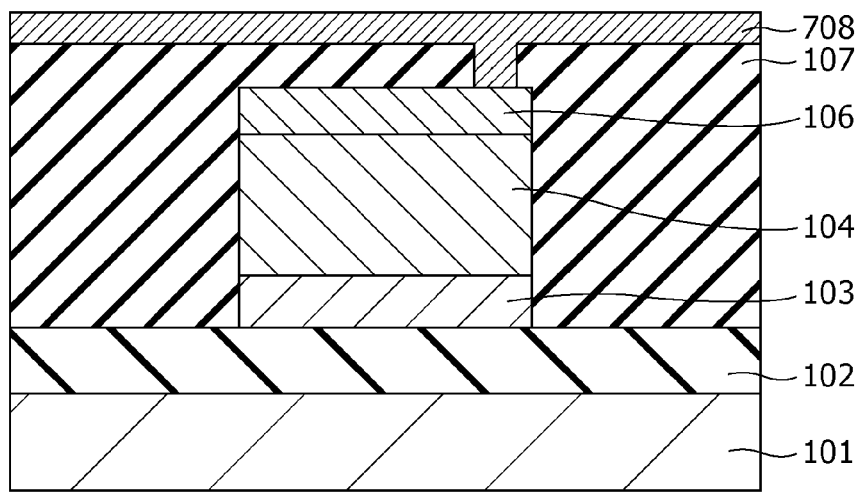
FIG. 2E is a cross-sectional view illustrating the method of producing the gas sensor according to First Embodiment.
Figure 2F:
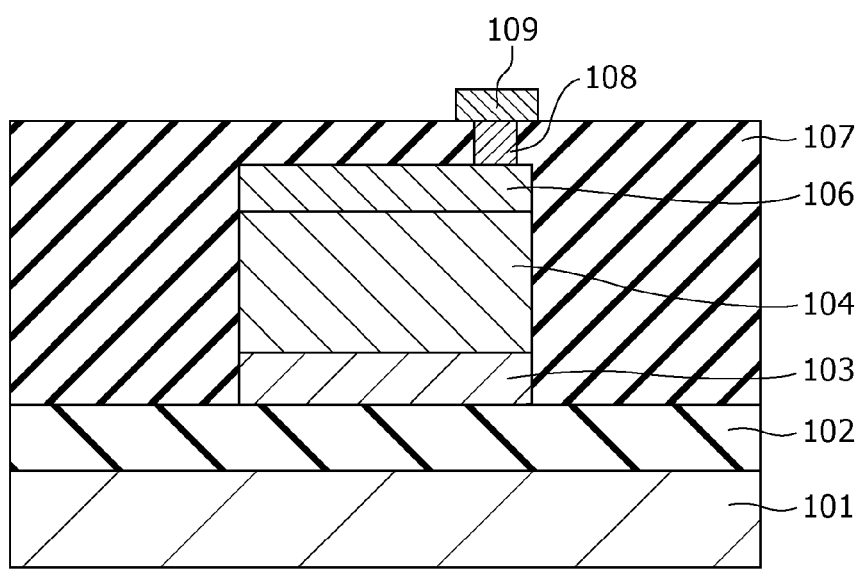
FIG. 2F is a cross-sectional view illustrating the method of producing the gas sensor according to First Embodiment.

Subsequently, as shown in FIG. 2E, a conductor film 708 is formed on the upper surface of the interlayer insulating film 107 and the inside of the via hole 107b so as to fill the via hole 107b. Then, as shown in FIG. 2F, the conductor film 708 on the interlayer insulating film 107 is removed by chemical mechanical planarization (CMP) to form a via 108 in the via hole 107b. Another conductor film is further formed on the interlayer insulating film 107 and is patterned to form a wiring conductor 109 connected to the via 108.

Figure 2G:
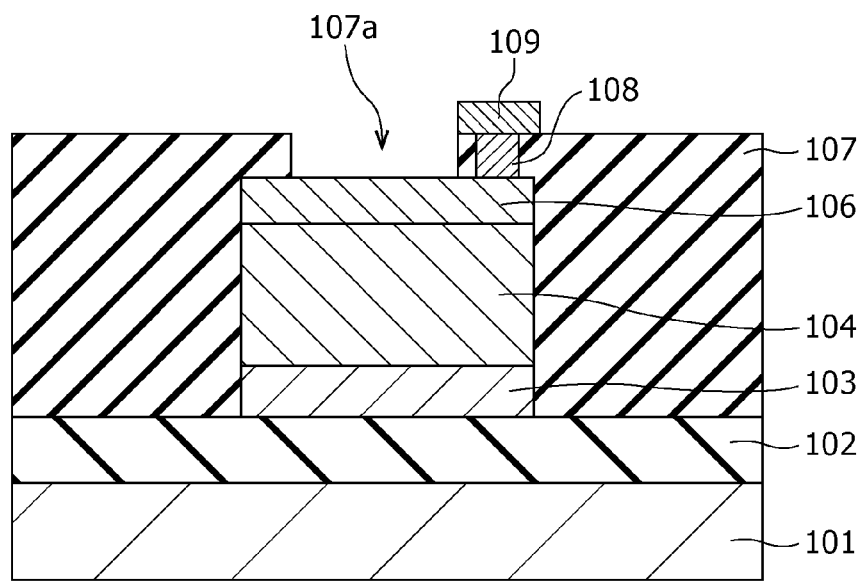
FIG. 2G is a cross-sectional view illustrating the method of producing the gas sensor according to First Embodiment.

Subsequently, as shown in FIG. 2G, an opening 107a is formed in the interlayer insulating film 107 by etching such that a part of the upper surface of the second electrode 106 is exposed.

Subsequently, a local region 105 shown in FIG. 1A is formed in the gas-sensitive resistive film 104 by applying an initial break voltage between the first electrode 103 and the second electrode 106. A gas sensor 100 is thus accomplished by the process described above.

Herein, an example of the resistance change characteristics by voltage application to the gas sensor 100 will be described by the results of actual measurement using a sample element. The resistance change characteristics by hydrogen-containing gas in the gas sensor 100 will be described later.

Figure 3:
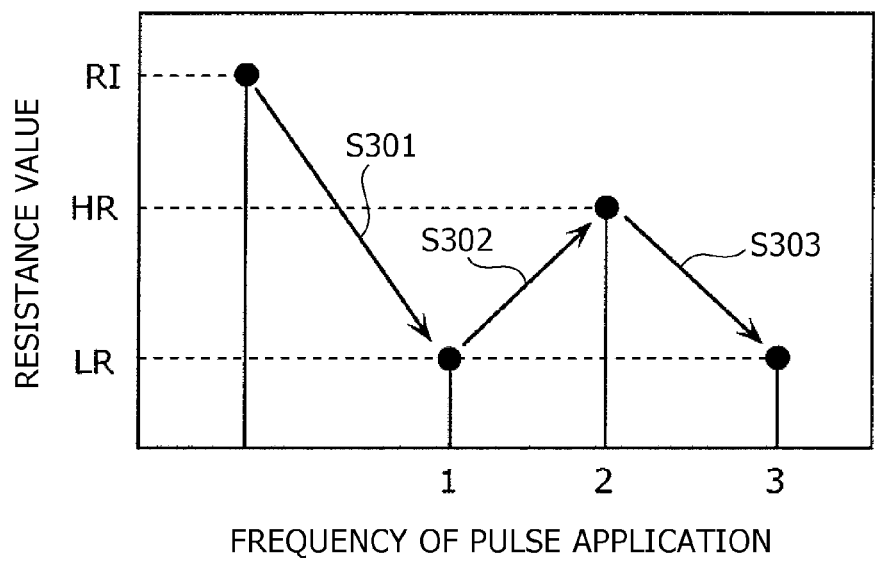
FIG. 3 is a diagram showing the state transition of the gas sensor according to First Embodiment.

FIG. 3 is a graph showing the resistance change characteristics actually measured with a sample element.

In the gas sensor 100, which is the sample element giving the results of measurement shown in FIG. 3, the first electrode 103, the second electrode 106, and the gas-sensitive resistive film 104 each have a size of 0.5 µm×0.5 µm (area: 0.25 µm$^2$); the composition of tantalum oxide represented by TaO$_y$ contained in the gas-sensitive resistive film 104 is adjusted such that y denotes 2.47; and the gas-sensitive resistive film 104 has a thickness of 5 nm. In this gas sensor 100, when a read-out voltage (e.g., 0.4 V) is applied between the first electrode 103 and the second electrode 106, the initial resistance value RI is about $10^7$ to $10^8 \Omega$.

As shown in FIG. 3, if the gas sensor 100 has an initial resistance value RI higher than the resistance value HR in a high resistance state, the resistance value changes to the low resistance value LR by applying an initial break voltage between the first electrode 103 and the second electrode 106 (step S301). The resistance value of the gas-sensitive resistive film 104 is then changed as shown in FIG. 3 by alternately applying, for example, two kinds of voltage pulses having different polarities, i.e., a positive voltage pulse and a negative voltage pulse, and each having a pulse width of 100 ns, as a write-in voltage, between the first electrode 103 and the second electrode 106 of the gas sensor 100.

That is, the resistance value of the gas-sensitive resistive film 104 is increased from the low resistance value LR to the high resistance value HR by applying a positive voltage pulse as the write-in voltage between the electrodes (step S302), and the resistance value of the gas-sensitive resistive film 104 is decreased from the high resistance value HR to the low resistance value LR by applying a negative voltage pulse as the write-in voltage between the electrodes (step S303). The polarity of a voltage pulse is "positive" when the potential of the second electrode 106 is higher than that of the first electrode 103 as a reference, and is "negative" when the potential of the second electrode 106 is lower than that of the first electrode 103 as a reference.

Hydrogen-containing gas can be detected utilizing the above-described resistance change characteristics caused by voltage application and using the gas sensor 100 set to a high resistance state by applying a positive voltage pulse between the first electrode 103 and the second electrode 106 before the start of monitoring of the hydrogen-containing gas. This allows more clear detection of a reduction in resistance value, compared with the detection of hydrogen-containing gas using the gas sensor 100 in a low resistance state and therefore improves the characteristics of detecting hydrogen-containing gas.

MODIFICATION EXAMPLE

Figure 4:
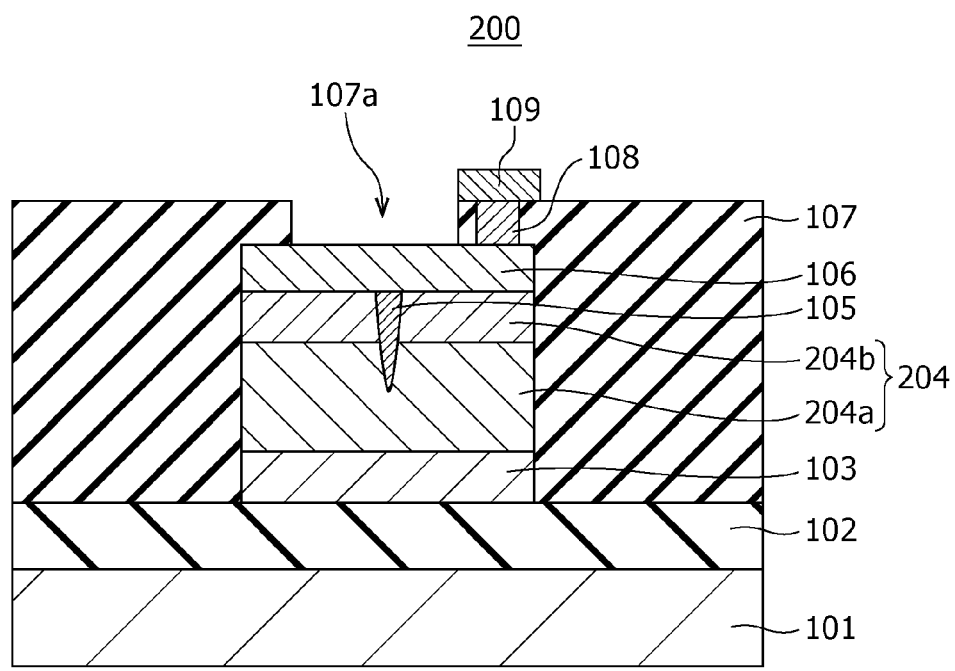
FIG. 4 is a cross-sectional view of a gas sensor according to a modification example of First Embodiment.

FIG. 4 is a cross-sectional view illustrating an exemplary configuration of a gas sensor according to a modification example of First Embodiment. Only the points different from the gas sensor 100 of First Embodiment will be described below.

The gas sensor 200 of this modification example differs from the gas sensor 100 of First Embodiment in that the gas-sensitive resistive film 204 includes two layers: a first metal oxide layer 204a being in contact with the first electrode 103 and a second metal oxide layer 204b stacked on the first metal oxide layer 204a and being in contact with the second electrode 106. The gas-sensitive resistive film 204 is not limited to of two layers and may include three or more metal oxide layers.

The first metal oxide layer 204a and the second metal oxide layer 204b contain a local region 105 that reversibly changes the degree of oxygen deficiency depending on application of an electric pulse and the presence or absence of hydrogen-containing gas. The local region 105 at least passes through the second metal oxide layer 204b and is in contact with the second electrode 106.

In other words, the gas-sensitive resistive film 204 has a layered structure at least composed of a first metal oxide layer 204a containing a first metal oxide and a second metal oxide layer 204b containing a second metal oxide. The first metal oxide layer 204a is disposed between the first electrode 103 and the second metal oxide layer 204b, and the second metal oxide layer 204b is disposed between the first metal oxide layer 204a and the second electrode 106.

The second metal oxide layer 204b may have a thickness smaller than that of the first metal oxide layer 204a. In this case, a structure in which the local region 105 is not in contact with the first electrode 103 can be easily formed. The metal oxide contained in the second metal oxide layer 204b may have a degree of oxygen deficiency smaller than that of the metal oxide contained in the first metal oxide layer 204a. In this case, since the second metal oxide layer 204b has a resistance value higher than that of the first metal oxide layer 204a, most of the voltage applied to the gas-sensitive resistive film 204 is applied to the second metal oxide layer 204b. This configuration can reduce, for example, the initial break voltage necessary for forming the local region 105.

In the present specification, if the metal contained in the first metal oxide layer 204a and the metal contained in the second metal oxide layer 204b are the same, the term "oxygen content" may be used instead of the term "degree of oxygen deficiency". "High oxygen content" corresponds to "low degree of oxygen deficiency", and "low oxygen content" corresponds to "high degree of oxygen deficiency".

However, as described later, the gas-sensitive resistive film 204 according to this embodiment is not limited to the case that the metal contained in the first metal oxide layer 204a and the metal contained in the second metal oxide layer 204b are the same. The metal contained in the first metal oxide layer 204a and the metal contained in the second metal oxide layer 204b may be different from each other. That is, the first metal oxide layer 204a and the second metal oxide layer 204b may contain different metal oxides.

If the first metal contained in the first metal oxide layer 204a and the second metal contained in the second metal oxide layer 204b are the same, the oxygen content has a corresponding relationship with the degree of oxygen deficiency. That is, when the oxygen content of the second metal oxide contained in the second metal oxide layer 204b is larger than that of the first metal oxide contained in the first metal oxide layer 204a, the second metal oxide has a degree of oxygen deficiency lower than that of the first metal oxide.

The gas-sensitive resistive film 204 includes a local region 105 in the vicinity of the interface between the first metal oxide layer 204a and the second metal oxide layer 204b. The degree of oxygen deficiency of the metal oxide contained in the local region 105 is higher than that of the metal oxide contained in the second metal oxide layer 204b and is different from that of the metal oxide contained in the first metal oxide layer 204a.

The local region 105 is formed in the gas-sensitive resistive film 204 by applying an initial break voltage between the first electrode 103 and the second electrode 106. Herein, the initial break voltage has an absolute value larger than that of the voltage that is applied between the first electrode 103 and the second electrode 106 for reversibly transiting the gas-sensitive resistive film 204 between a high resistance state and a low resistance state. The initial break voltage may be lower than the above-mentioned voltage applied for reversible transition between the high resistance state and the low resistance state, and may be applied between the first electrode 103 and the second electrode 106 repeatedly or continuously for a predetermined period of time. The application of the initial break voltage forms a local region 105 that is in contact with the second electrode 106, passes through the second metal oxide layer 204b, partially penetrates into the first metal oxide layer 204a, and is not in contact with the first electrode 103.

An example of evaluation of the resistance change characteristics by hydrogen-containing gas in the thus-configured gas sensor 200 will be described.

Figure 5A:
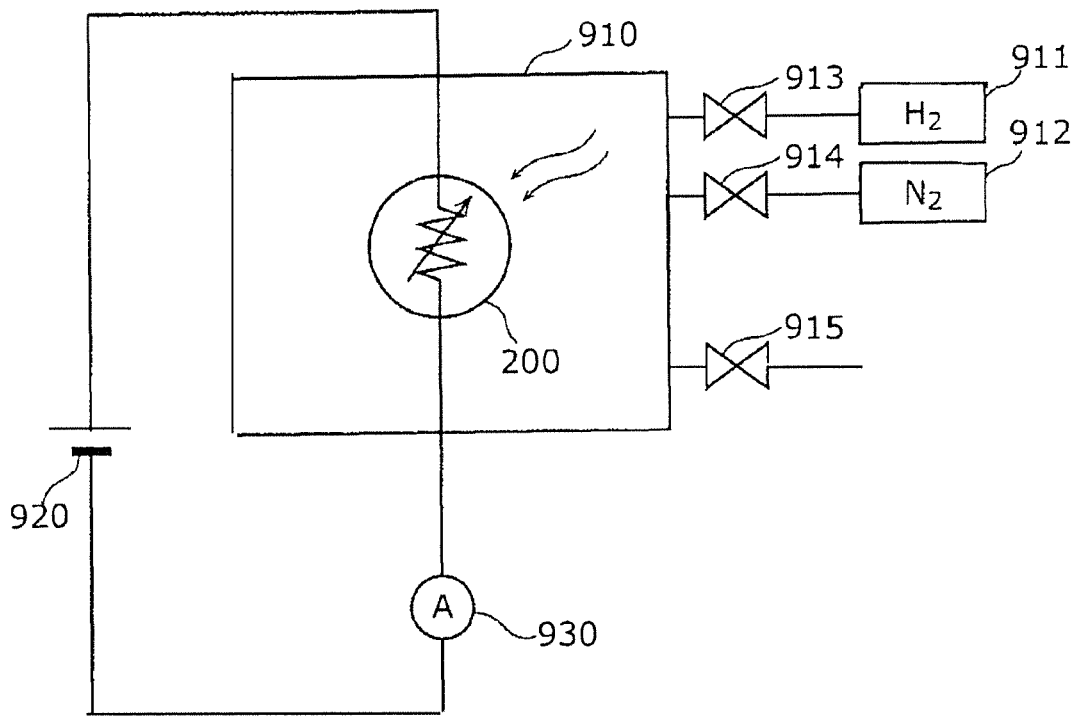
FIG. 5A is a diagram showing an evaluation system of the gas sensor according to the modification example of First Embodiment.

FIG. 5A is a block diagram showing an example of an evaluation system used for evaluating the gas sensor 200. The evaluation system 900 shown in FIG. 5A includes an airtight container 910 storing the gas sensor 200, a power supply 920, and a current meter 930. The airtight container 910 is connected to a hydrogen cylinder 911 and a nitrogen cylinder 912 through introduction valves 913 and 914, respectively, and is configured such that the gas inside the airtight container 910 can be exhausted through an exhaust valve 915.

Figure 5B:
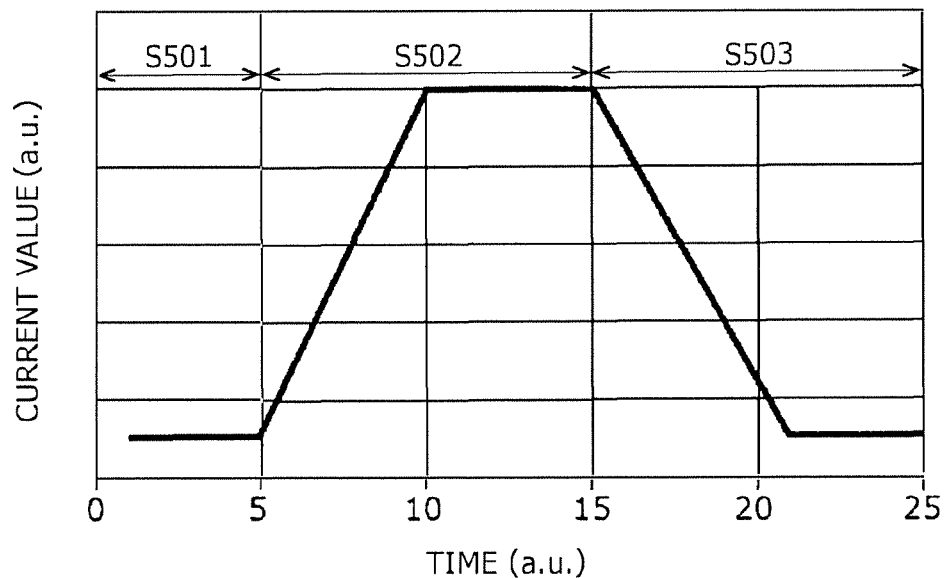
FIG. 5B is a diagram showing the results of evaluation of the gas sensor according to the modification example of First Embodiment.

FIG. 5B is a graph showing an example of evaluation of the gas sensor 200. The horizontal axis indicates the time (a.u.), and the vertical axis indicates the current value (a.u.) flowing between the first electrode 103 and the second electrode 106. In an experiment, nitrogen gas was introduced into the airtight container 910 accommodating the gas sensor 200. The nitrogen gas was then replaced by hydrogen gas, and the hydrogen gas was further replaced by nitrogen gas.

FIG. 5B shows the results of the above experiment. The horizontal axis shows the three periods for carrying out the former introduction of nitrogen (step S501), the introduction of hydrogen (step S502), and the latter introduction of nitrogen (step S503). It is demonstrated that the current value started to increase after the change of the introduction gas from nitrogen gas to hydrogen gas. It is also demonstrated that the current started to decrease after the change of the introduction gas from hydrogen gas to nitrogen gas.

In this example of evaluation, a gas sensor 200 of which the local region 105 was set to a high resistance state in advance by applying a certain voltage between the first electrode 103 and the second electrode 106 was used. In the monitoring behavior for hydrogen-containing gas, a current of 10 to 20 μA flowed between the first electrode 103 and the second electrode 106 in the state of detecting hydrogen gas by applying a detection voltage of 0.6 V between the first electrode 103 and the second electrode 106. It is therefore demonstrated that the gas sensor 200 can monitor hydrogen-containing gas with a very small power consumption of 0.006 to 0.012 mW.

Application of a detection voltage of 0.4 V between the first electrode 103 and the second electrode 106 did not cause a change in resistance due to hydrogen gas, resulting in no detection of the hydrogen gas. This suggests that the heat generation of the local region 105 by application of a detection voltage of 0.4 V is insufficient for accelerating the catalytic action of the second electrode 106 and that application of a detection voltage of 0.6 V is necessary for detecting hydrogen gas.

From this result, the present inventors presume the mechanism of detecting hydrogen gas by the gas sensor 200 as follows.

Hydrogen-containing gas brought into contact with the second electrode 106 releases hydrogen atoms by the catalytic action of the second electrode 106. The released hydrogen atoms diffuse in the second electrode 106 for maintaining an equilibrium state and reach the local region 105.

It is presumed that the hydrogen atoms cause a reduction reaction of the metal oxide in the local region 105 to increase the degree of oxygen deficiency of the metal oxide contained in the local region 105; as a result, the filaments in the local region 105 are readily connected to one another to reduce the resistance value of the local region 105; and as a result, the current flowing between the first electrode 103 and the second electrode 106 is increased.

In contrast, if the hydrogen-containing gas in the vicinity of the second electrode 106 disappears, hydrogen atoms become hydrogen molecules in the vicinity of the surface of the second electrode 106 for maintaining an equilibrium state, and the hydrogen molecules go out to the outside from the surface of the second electrode 106.

This causes a reaction of decomposing water molecules generated in the local region 105 into hydrogen atoms and oxygen atoms by a reduction reaction. The generated hydrogen atoms return to the inside of the second electrode 106. The generated oxygen atoms compensate for the oxygen deficiency to decrease the degree of oxygen deficiency of the metal oxide contained in the local region 105.

It is presumed that as a result, the filaments in the local region 105 are hardly connected to one another to increase the resistance value. As a result, the current flowing between the first electrode 103 and the second electrode 106 is decreased.

It is presumed that the above-described behavior is not limited to the gas sensor 200 and also occurs in the gas sensor 100 and other gas sensors described below, which include main sections having substantially the same structures as that of the gas sensor 200. It is also presumed that the above-described behavior is not limited to the case that the gas to be brought into contact with the second electrode 106 is hydrogen gas and also occurs, for example, in the case that the gas is hydrogen-containing gas, such as methane and alcohol.

As described above, the present embodiment can provide a gas sensor having excellent power-saving properties that can generate heat by only the current for detecting the resistance state and can detect hydrogen-containing gas without heating with a separate heater.

(Second Embodiment)
[Configuration of Gas Sensor]

The gas sensor according to Second Embodiment has a metal-insulating film-metal (MIM) structure formed by stacking a gas-sensitive resistive film serving as a metal oxide layer and metal films, as in the gas sensor according to First Embodiment. The gas sensor can detect hydrogen-containing gas, without heating with a heater, by utilizing self-heating and gas sensitivity of a local region, which is a part of the gas-sensitive resistive film. Herein, the term "hydrogen-containing gas" is a generic name for gas composed of molecules including hydrogen atoms, and examples of the hydrogen-containing gas include hydrogen, methane, and alcohol.

Figure 6A:
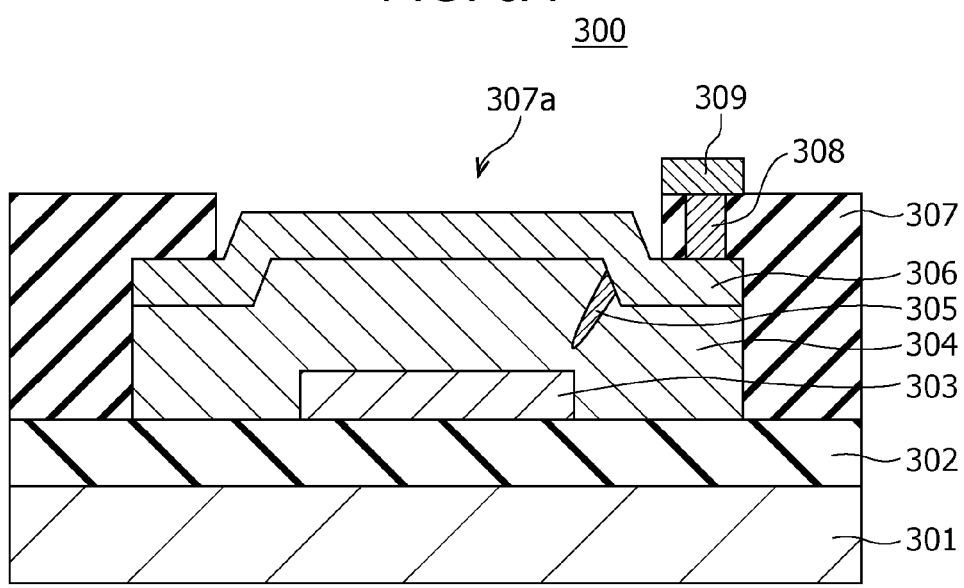
FIG. 6A is a cross-sectional view of a gas sensor according to Second Embodiment.

FIG. 6A is a cross-sectional view illustrating an exemplary configuration of a gas sensor 300 according to Second Embodiment.

Figure 6B:
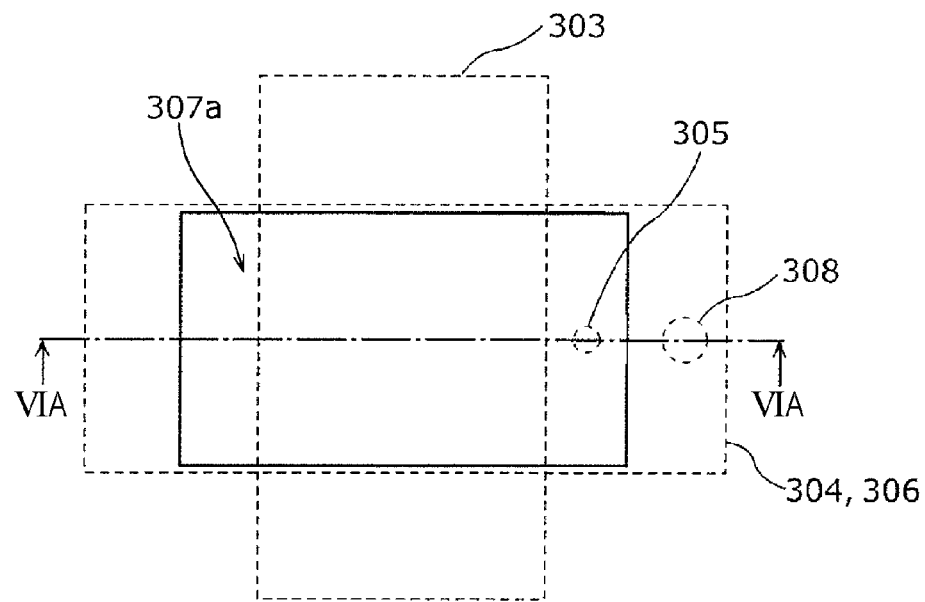
FIG. 6B is a top view of the gas sensor according to Second Embodiment.

FIG. 6B is a top view illustrating an exemplary configuration of the gas sensor 300 according to Second Embodiment. The cross section shown in FIG. 6A is that viewed from the direction indicated by the arrows on the cutting-plane line VIA-VIA of FIG. 6B.

The gas sensor 300 includes a substrate 301; an insulating film 302 disposed on the substrate 301; and a first electrode 303, a second electrode 306, a gas-sensitive resistive film 304 disposed between the first electrode 303 and the second electrode 306, an interlayer insulating film 307, a via 308, and a wiring conductor 309 disposed above the insulating film 302. In the first electrode 303, the lower surface is a first main surface, and the upper surface is a second main surface. In the second electrode 306, the lower surface is a third main surface, and the upper surface is a fourth main surface. The first electrode 303 and the second electrode 306 are disposed such that the second main surface faces at least a part of the third main surface. The gas-sensitive resistive film 304 is disposed so as to be in contact with the second main surface of the first electrode 303 and the third main surface of the second electrode 306.

The interlayer insulating film 307 is provided with an opening 307a for bringing the second electrode 306 into contact with the gas as an object to be tested. In other words, while the interlayer insulating film 307 covers a part of the second electrode 306 and the gas-sensitive resistive film 304, at least a part of the upper surface of the second electrode 306 is not covered by the interlayer insulating film 307 and is exposed to the gas as an object to be tested.

The area of the gas-sensitive resistive film 304 being in contact with the first electrode 303 is smaller than the area of the gas-sensitive resistive film 304 being in contact with the second electrode 306.

The gas-sensitive resistive film 304 is a layer, as in the gas-sensitive resistive film 104 according to First Embodiment described above, disposed between the first electrode 303 and the second electrode 306 and reversibly transitionable between a high resistance state and a low resistance state. The resistance state of the gas-sensitive resistive film 304 changes depending on the voltage applied between the first electrode 303 and the second electrode 306 and the presence or absence of hydrogen-containing gas in the gas that is brought into contact with the second electrode 306.

The gas-sensitive resistive film 304 contains therein a local region 305 being in contact with the second electrode 306 and not being in contact with the first electrode 303. The metal oxide contained in the local region 305 reversibly changes the degree of oxygen deficiency depending on the electric pulse provided between the first electrode 303 and the second electrode 306. The metal oxide contained in the local region 305 has a degree of oxygen deficiency larger than that of the metal oxide contained in the portion other than the local region 305 in the gas-sensitive resistive film 304. The local region 305 is a minute region containing a filament consisting of an oxygen defect site. The filament functions as a conductive path.

The interlayer insulating film 307 is provided with a via 308 in the portion covering the second electrode 306. The via 308 passes through the interlayer insulating film 307 and reaches the second electrode 306. A wiring conductor 309 is disposed on the via 308.

The thus-configured gas sensor 300 can achieve the following effects.

The local region 305 is easily formed in the region where the electric field is concentrated in the gas-sensitive resistive film 304 by applying an initial break voltage. Accordingly, if the first electrode 303 lies below the via 308, the local region 305 is relatively easily formed in a region directly under the via 308. For example, if the local region 305 is formed directly under the upper structures such as the via 308, the hydrogen atoms released from the hydrogen-containing gas at the second electrode 306 cannot reach the local region 305 within a short period of time, resulting in a risk of deteriorating the detection sensitivity and the response time.

In contrast, in the gas sensor 300 according to Second Embodiment, since the area of the gas-sensitive resistive film 304 being in contact with the first electrode 303 is smaller than the area of the gas-sensitive resistive film 304 being in contact with the second electrode 306, the outline of the first electrode 303 viewed from the top can be disposed in a desired position within the second electrode 306. Accordingly, the local region 305 can be formed according to the position of the outline of the first electrode 303 while avoiding, for example, the position having a risk of deteriorating the detection sensitivity and the response time, i.e., portions directly under the upper structures such as the via 308 for connection.

The hydrogen atoms released from the hydrogen-containing gas at the second electrode 306 can reach the local region 305 within a short time by forming the local region 305, for example, in the region directly under the opening 307a, avoiding the region directly under the via 308. That is, in the configuration of the gas sensor 300, the time that is necessary for hydrogen atoms to reach the local region 305 from the surface of the second electrode 306 is shorter than the time in the case of forming the local region 305 directly under the via 308. As a result, the resulting gas sensor 300 can have excellent responsiveness.

The phenomenon of changing the resistance in the gas sensor 300 and the mechanism of detecting hydrogen are the same as those in the gas sensor 100 of First Embodiment, and the descriptions thereof are omitted herein.

[Method of Producing Gas Sensor and Behavior]

An example of a method of producing the gas sensor 300 will then be described with reference to FIGS. 7A to 7J.

Figure 7A:
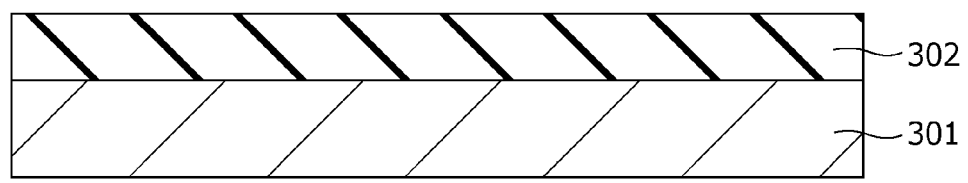
FIG. 7A is a cross-sectional view illustrating a method of producing the gas sensor according to Second Embodiment.

First, as shown in FIG. 7A, an insulating film 302 having a thickness of 200 nm is formed on a substrate 301, for example, of single crystal silicon by a thermal oxidation method.

Figure 7B:
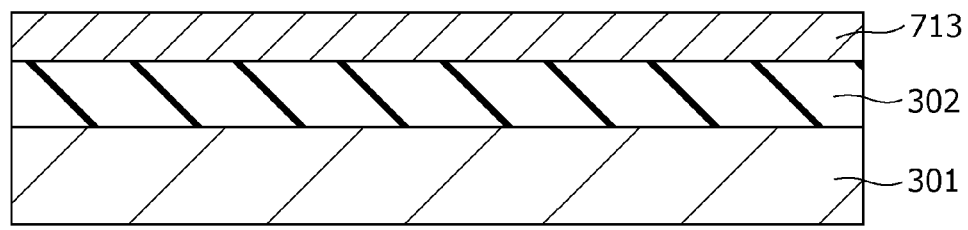
FIG. 7B is a cross-sectional view illustrating the method of producing the gas sensor according to Second Embodiment.

Subsequently, as shown in FIG. 7B, as a conductor film 713 to be formed into a first electrode 303, for example, a Pt film having a thickness of 100 nm is formed on the insulating film 302 by sputtering. In addition, an adhesion layer of, for example, Ti or TiN may be formed between the conductor film 713 and the insulating film 302 by sputtering. A photoresist mask (not shown) is then formed on the conductor film 713 by a photolithography process.

Figure 7C:
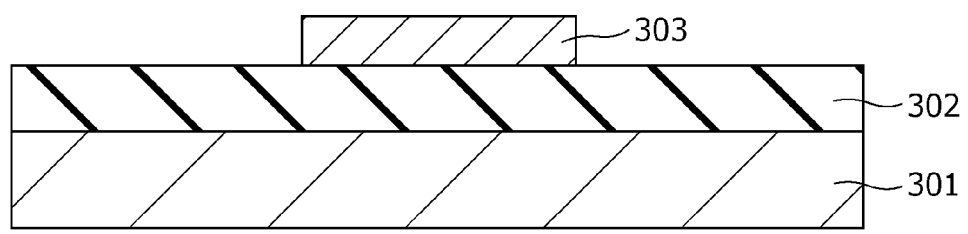
FIG. 7C is a cross-sectional view illustrating the method of producing the gas sensor according to Second Embodiment.

Then, as shown in FIG. 7C, the first electrode 303 is formed by dry etching using the mask.

Figure 7D:
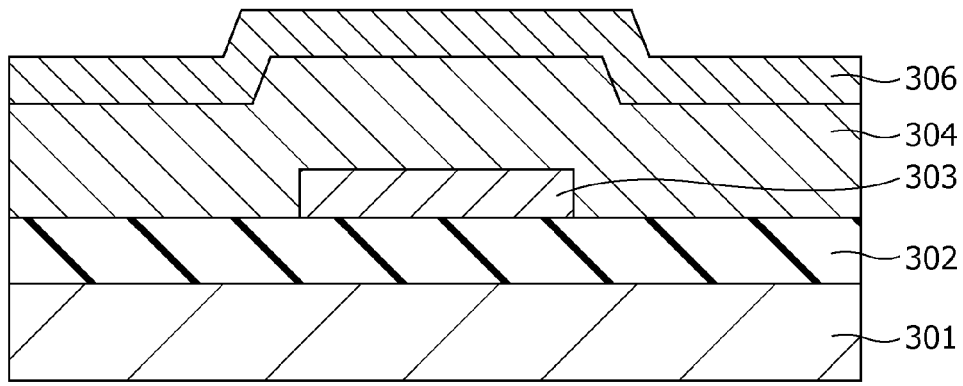
FIG. 7D is a cross-sectional view illustrating the method of producing the gas sensor according to Second Embodiment.

Then, as shown in FIG. 7D, a metal oxide layer in an oxygen deficiency state, which is formed into a gas-sensitive resistive film 304, is formed on the first electrode 303 by reactive sputtering using, for example, a Ta target. Herein, regarding the thickness of the gas-sensitive resistive film 304, a too large thickness causes disadvantages of, for example, giving a too high initial resistance value, and a too small thickness causes a disadvantage of not providing a stable resistance change. For these reasons, the thickness of gas-sensitive resistive film 304 may be about 1 nm or more and about 8 nm or less.

A second electrode 306 of, for example, a Pt film having a thickness of 150 nm is then formed on the gas-sensitive resistive film 304 by sputtering.

Figure 7E:
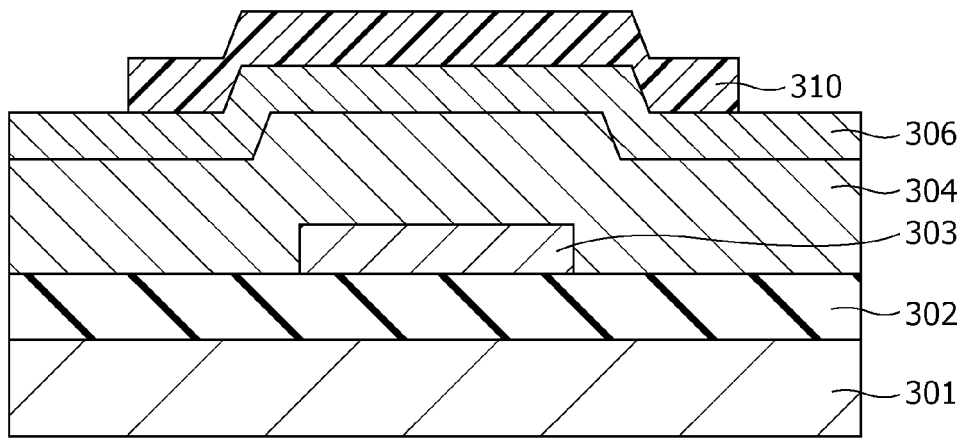
FIG. 7E is a cross-sectional view illustrating the method of producing the gas sensor according to Second Embodiment.

Then, as shown in FIG. 7E, a photoresist mask 310 is formed on the second electrode 306 by a photolithography process.

Figure 7F:
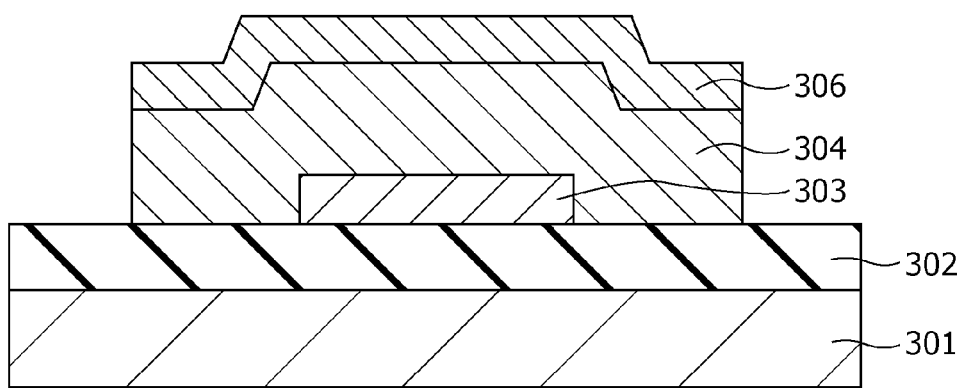
FIG. 7F is a cross-sectional view illustrating the method of producing the gas sensor according to Second Embodiment.

Then, as shown in FIG. 7F, the gas-sensitive resistive film 304 and the second electrode 306 are formed into the shape of an element by dry etching using the mask 310.

The above-described process forms a structure in which the area of the gas-sensitive resistive film 304 being in contact with the first electrode 303 is smaller than the area of the gas-sensitive resistive film 304 being in contact with the second electrode 306, and arranges the outline of the first electrode 303 within the second electrode 306 viewed from the top.

Figure 7G:
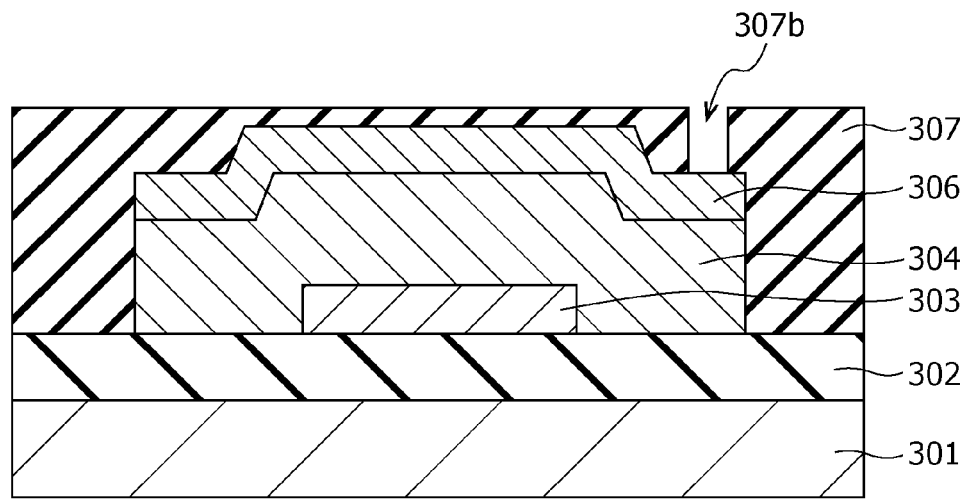
FIG. 7G is a cross-sectional view illustrating the method of producing the gas sensor according to Second Embodiment.

As shown in FIG. 7G, an interlayer insulating film 307 is then formed so as to cover the insulating film 302, the gas-sensitive resistive film 304, and the second electrode 306. Then, a via hole 307b reaching a part of the upper surface of the second electrode 306 is formed in the interlayer insulating film 307 by etching.

Figure 7H:
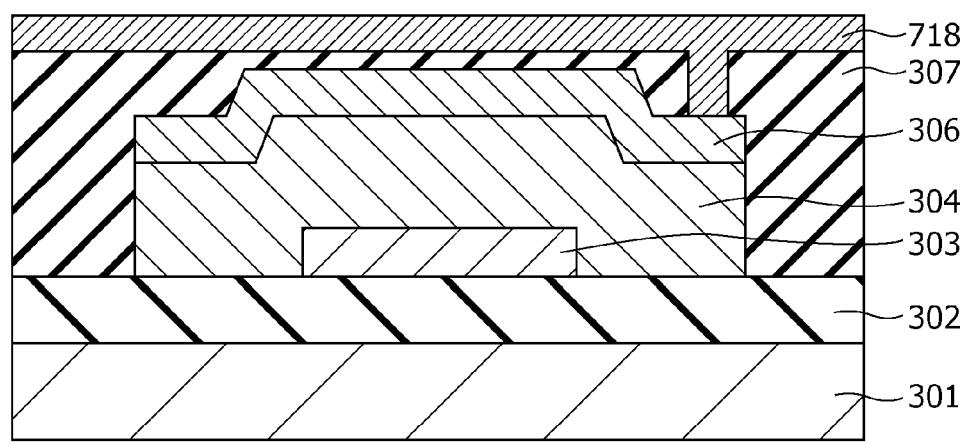
FIG. 7H is a cross-sectional view illustrating the method of producing the gas sensor according to Second Embodiment.
Figure 7I:
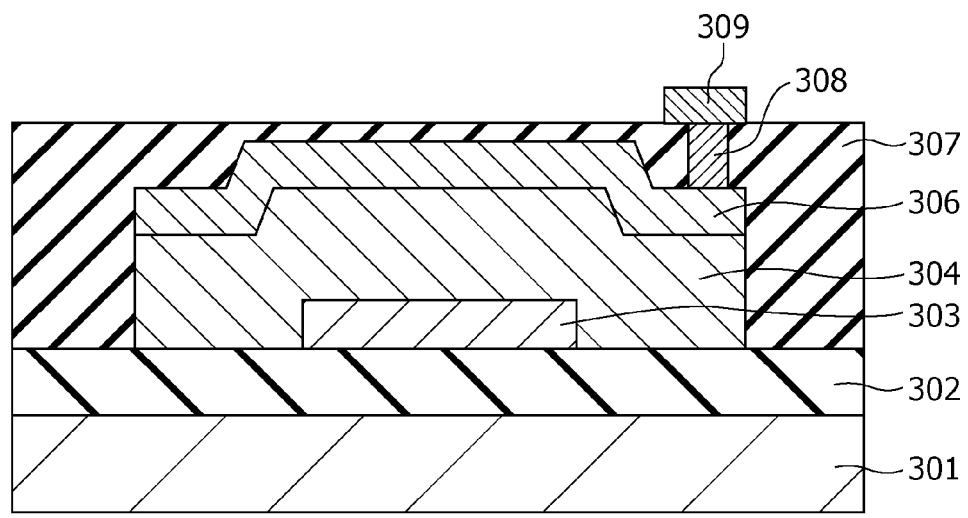
FIG. 7I is a cross-sectional view illustrating the method of producing the gas sensor according to Second Embodiment.

Then, as shown in FIG. 7H, a conductor film 718 is formed on the upper surface of the interlayer insulating film 307 and the inside of the via hole 307b so as to fill the via hole 307b. Then, as shown in FIG. 7I, the conductor film 718 on the interlayer insulating film 307 is removed by CMP to form a via 308 in the via hole 307b. Another conductor film is further formed on the interlayer insulating film 307 and is patterned to form a wiring conductor 309 connected to the via 308.

Figure 7J:
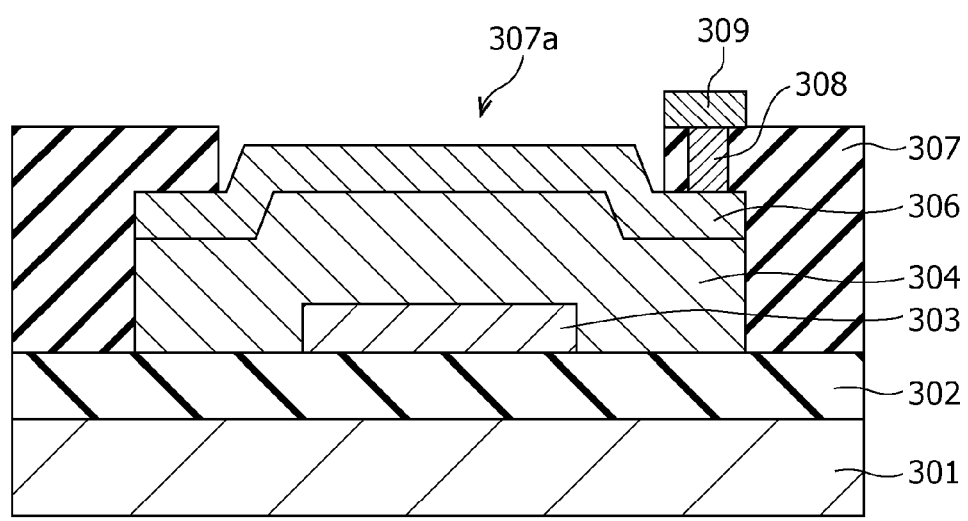
FIG. 7J is a cross-sectional view illustrating the method of producing the gas sensor according to Second Embodiment.

Then, as shown in FIG. 7J, an opening 307a is formed in the interlayer insulating film 307 by etching such that a part of the upper surface of the second electrode 306 is exposed.

Subsequently, a local region 305 is formed in the gas-sensitive resistive film 304 at the portion corresponding to the outline of the first electrode 303 in a planar view by applying an initial break voltage between the first electrode 303 and the second electrode 306. A gas sensor 300 shown in FIG. 6A is thus accomplished.

The resistance change characteristics by voltage application to the thus-configured gas sensor 300 are substantially the same as those by voltage application to the gas sensor 100 shown in FIG. 3. In also the gas sensor 300, the resistance change due to hydrogen-containing gas is caused by the same mechanism as that described for the gas sensor 100. Accordingly, the gas sensor 300 can detect hydrogen-containing gas with a low power consumption.

Modification Example 1

Figure 8:
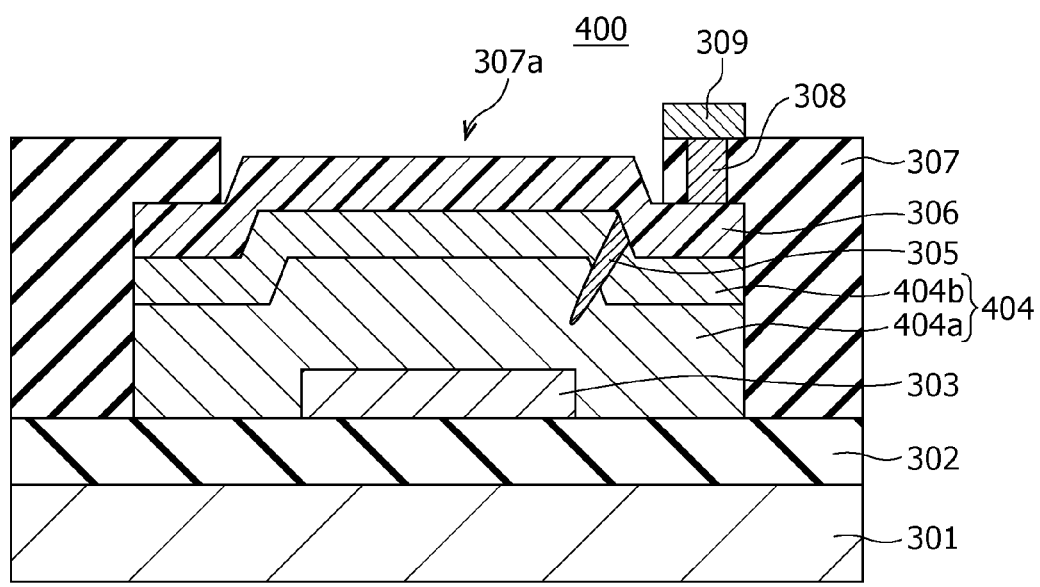
FIG. 8 is a cross-sectional view of a gas sensor according to modification example 1 of Second Embodiment.

FIG. 8 is a cross-sectional view illustrating an exemplary configuration of a gas sensor 400 according to modification example 1 of Second Embodiment. Only the points different from the gas sensor 300 of Second Embodiment will be described below.

The gas sensor 400 of modification example 1 differs from the gas sensor 300 of Second Embodiment in that the gas-sensitive resistive film 404 includes two layers: a first metal oxide layer 404a being in contact with the first electrode 303 and a second metal oxide layer 404b stacked on the first metal oxide layer 404a and being in contact with the second electrode 306. The gas-sensitive resistive film 404 is not limited to of two layers and may include three or more metal oxide layers.

The first metal oxide layer 404a and the second metal oxide layer 404b contain a local region 305 that reversibly changes the degree of oxygen deficiency depending on application of an electric pulse and the presence or absence of hydrogen-containing gas. The local region 305 at least passes through the second metal oxide layer 404b and is in contact with the second electrode 306. The metal oxide contained in the local region 305 has a degree of oxygen deficiency larger than that of the metal oxide contained in the second metal oxide layer 404b.

In other words, the gas-sensitive resistive film 404 has a layered structure at least composed of a first metal oxide layer 404a containing a first metal oxide and a second metal oxide layer 404b containing a second metal oxide. The first metal oxide layer 404a is disposed between the first electrode 303 and the second metal oxide layer 404b, and the second metal oxide layer 404b is disposed between the first metal oxide layer 404a and the second electrode 306.

The second metal oxide layer 404b may have a thickness smaller than that of the first metal oxide layer 404a. In such a case, a structure of the local region 305 not being in contact with the first electrode 303 can be easily formed. The metal oxide contained in the second metal oxide layer 404b may have a degree of oxygen deficiency smaller than that of the metal oxide contained in the first metal oxide layer 404a. In this case, since the second metal oxide layer 404b has a resistance value higher than that of the first metal oxide layer 404a, most of the voltage applied to the gas-sensitive resistive film 404 is applied to the second metal oxide layer 404b. This configuration can reduce, for example, the initial break voltage necessary for forming the local region 305.

The gas-sensitive resistive film 404 is not limited to the cases that the first metal oxide layer 404a and the second metal oxide layer 404b contain the same metals. The metals contained in the first metal oxide layer 404a and the second metal oxide layer 404b may be different from each other. That is, the first metal oxide layer 404a and the second metal oxide layer 404b may contain different metal oxides.

If the first metal contained in the first metal oxide layer 404a and the second metal contained in the second metal oxide layer 404b are the same, the oxygen content has a corresponding relationship with the degree of oxygen deficiency. That is, when the oxygen content of the second metal oxide contained in the second metal oxide layer 404b is higher than that of the first metal oxide contained in the first metal oxide layer 404a, the second metal oxide has a degree of oxygen deficiency lower than that of the first metal oxide.

The gas-sensitive resistive film 404 includes a logical region 305 in the vicinity of the interface between the first metal oxide layer 404a and the second metal oxide layer 404b. The degree of oxygen deficiency of the metal oxide contained in the local region 305 is larger than that of the metal oxide contained in the second metal oxide layer 404b and is different from that of the metal oxide contained in the first metal oxide layer 404a.

The local region 305 is formed in the gas-sensitive resistive film 404 by applying an initial break voltage between the first electrode 303 and the second electrode 306. Herein, the initial break voltage is the same as that in First Embodiment, and the description thereof is omitted. The application of the initial break voltage forms a local region 305 that is in contact with the second electrode 306, passes through the second metal oxide layer 404b, partially penetrates into the first metal oxide layer 404a, and is not in contact with the first electrode 303.

The thus-configured gas sensor 400 can generate heat by only the current for detecting the resistance state and can detect hydrogen-containing gas without heating with a separate heater.

Modification Example 2

Figure 9:
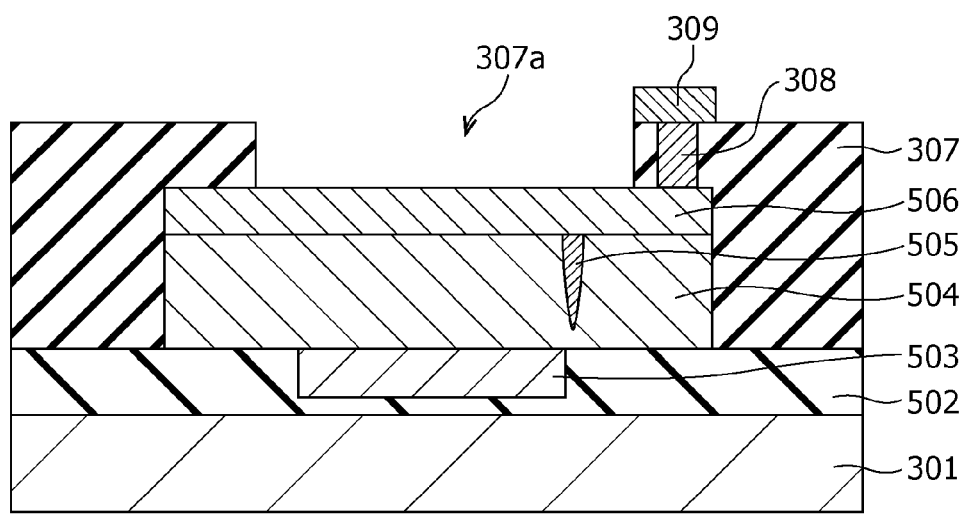
FIG. 9 is a cross-sectional view of a gas sensor according to modification example 2 of Second Embodiment.

FIG. 9 is a cross-sectional view illustrating an exemplary configuration of a gas sensor 500 according to modification example 2 of Second Embodiment. Only the points different from the gas sensor 300 of Second Embodiment will be described below.

The gas sensor 500 differs from the gas sensor 300 of Second Embodiment in that the first electrode 503 is embedded in the insulating film 502 and that the upper surface of the first electrode 503 and the upper surface of the insulating film 502 form a flush surface. The gas-sensitive resistive film 504 and the second electrode 506 above the first electrode 503 are formed in a flat plate-form by forming the upper surface of the first electrode 503 and the upper surface of the insulating film 502 on the same plane. In the first electrode 503, the lower surface is a first main surface, and the upper surface is a second main surface. In the second electrode 506, the lower surface is a third main surface, and the upper surface is a fourth main surface. The first electrode 503 and the second electrode 506 are disposed such that the second main surface faces at least a part of the third main surface. The gas-sensitive resistive film 504 is disposed so as to be in contact with the second main surface of the first electrode 503 and the third main surface of the second electrode 506. The metal oxide contained in the local region 505 reversibly changes the degree of oxygen deficiency depending on application of an electric pulse and the presence or absence of hydrogen-containing gas. The local region 505 is disposed so as to be in contact with the second electrode 506. The metal oxide contained in the local region 505 has a degree of oxygen deficiency larger than that of the metal oxide contained in the portion other than the local region 505 in the gas-sensitive resistive film 504. This local region 505 is a minute region containing a filament consisting of an oxygen defect site.

An example of a method of producing the gas sensor 500 of modification example 2 will be described with reference to FIGS. 10A to 10I.

Figure 10A:
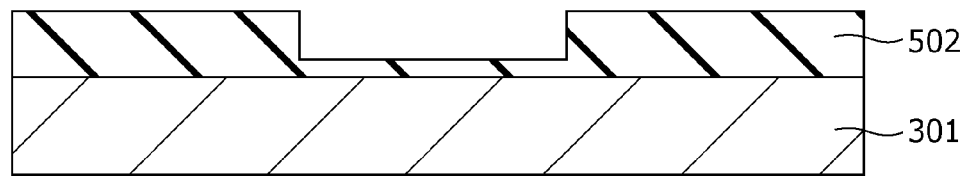
FIG. 10A is a cross-sectional view illustrating a method of producing the gas sensor according to modification example 2 of Second Embodiment.

First, as shown in FIG. 10A, an insulating film 502 having a thickness of 200 nm is formed on a substrate 301, for example, of single crystal silicon by a thermal oxidation method. A groove having a depth of 100 nm for embedding a first electrode 503 is then formed by a photography technique and a dry etching technique.

Figure 10B:
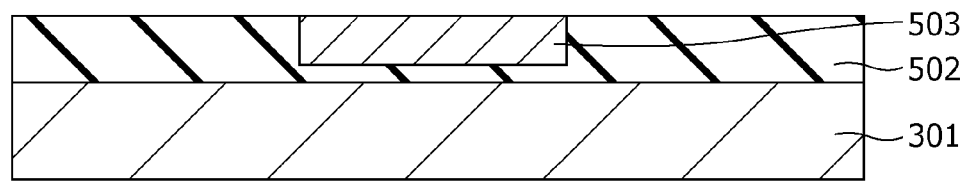
FIG. 10B is a cross-sectional view illustrating the method of producing the gas sensor according to modification example 2 of Second Embodiment.

As a conductor film to be formed into a first electrode 503, for example, a Pt film having a thickness of 200 nm is then formed on the insulating film 502 so as to fill the groove by sputtering. Subsequently, as shown in FIG. 10B, the Pt film on the upper surface of the insulating film 502 is removed by CMP while leaving the Pt film in the groove such that the upper surface of the insulating film 502 is flush with the upper surface of the first electrode 503. In addition, an adhesion layer of, for example, Ti or TiN may be formed between the first electrode 503 and the insulating film 502 by sputtering.

Figure 10C:
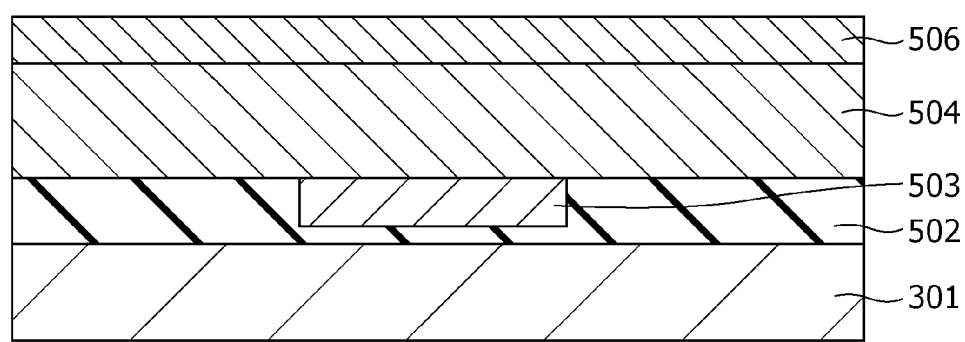
FIG. 10O is a cross-sectional view illustrating the method of producing the gas sensor according to modification example 2 of Second Embodiment.
FIG. 10D is a cross-sectional view illustrating the method of producing the gas sensor according to modification example 2 of Second Embodiment.
FIG. 10E is a cross-sectional view illustrating the method of producing the gas sensor according to modification example 2 of Second Embodiment.
FIG. 10F is a cross-sectional view illustrating the method of producing the gas sensor according to modification example 2 of Second Embodiment.
FIG. 10G is a cross-sectional view illustrating the method of producing the gas sensor according to modification example 2 of Second Embodiment.
FIG. 10H is a cross-sectional view illustrating the method of producing the gas sensor according to modification example 2 of Second Embodiment.
FIG. 10I is a cross-sectional view illustrating the method of producing the gas sensor according to modification example 2 of Second Embodiment.

Subsequently, as shown in FIG. 10C, a metal oxide layer in an oxygen deficiency state, which is formed into a gas-sensitive resistive film 504, is formed by reactive sputtering using, for example, a Ta target. Herein, regarding the thickness of the gas-sensitive resistive film 504, a too large thickness causes disadvantages of, for example, giving a too high initial resistance value, and a too small thickness causes a disadvantage of not providing a stable resistance change. For these reasons, the thickness of the gas-sensitive resistive film 504 may be about 1 nm or more and about 8 nm or less. Subsequently, for example, a Pt film having a thickness of 150 nm is formed as the second electrode 506 on the gas-sensitive resistive film 504 by sputtering.

Figure 10D:
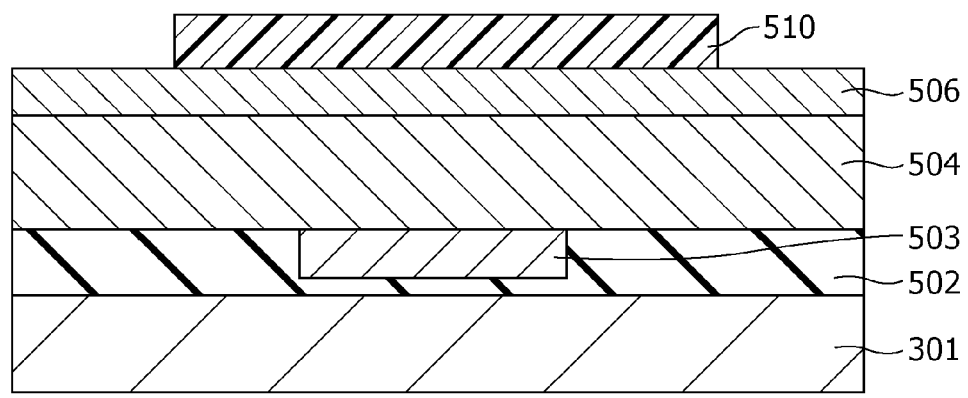

As shown in FIG. 10D, a photoresist mask 510 is then formed on the second electrode 506 by a photolithography process.

Figure 10E:
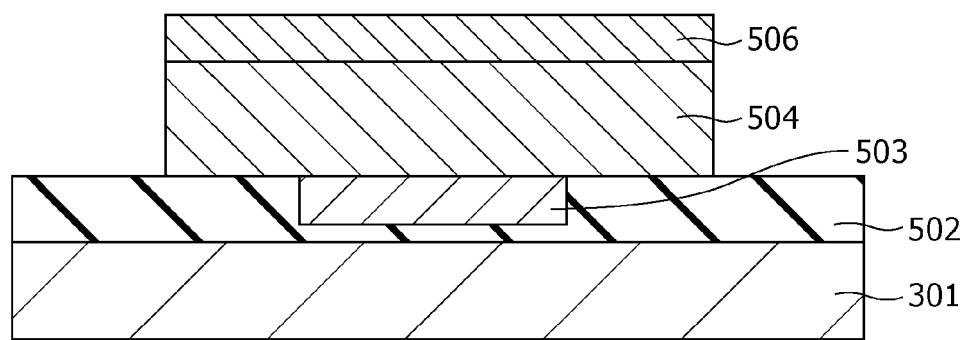

Subsequently, as shown in FIG. 10E, the gas-sensitive resistive film 504 and the second electrode 506 are formed into the shape of an element by dry etching using the mask 510.

Figure 10F:
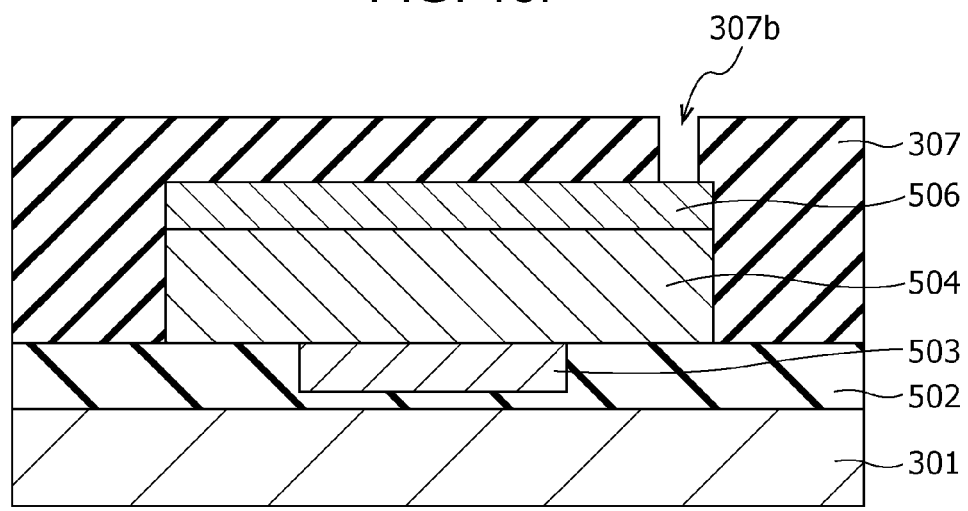

Subsequently, as shown in FIG. 10F, an interlayer insulating film 307 is formed so as to cover the insulating film 502, the gas-sensitive resistive film 504, and the second electrode 506. A via hole 307b reaching a part of the upper surface of the second electrode 506 is then formed in the interlayer insulating film 307 by etching.

Figure 10G:
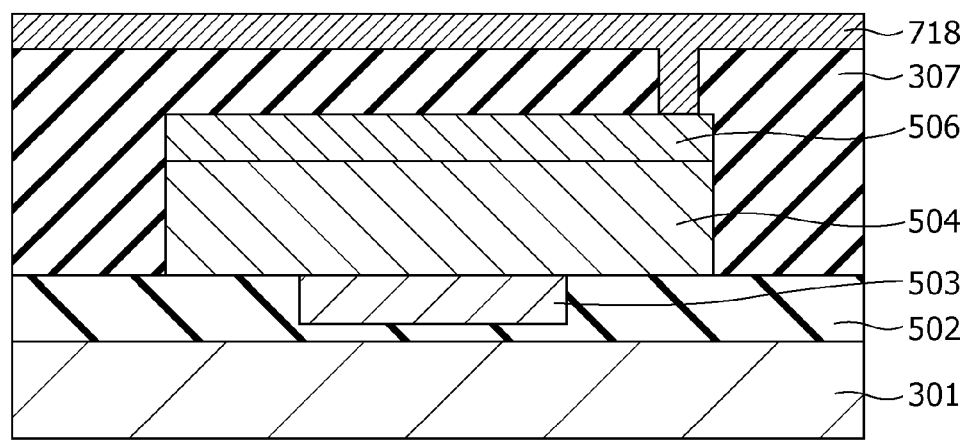
Figure 10H:
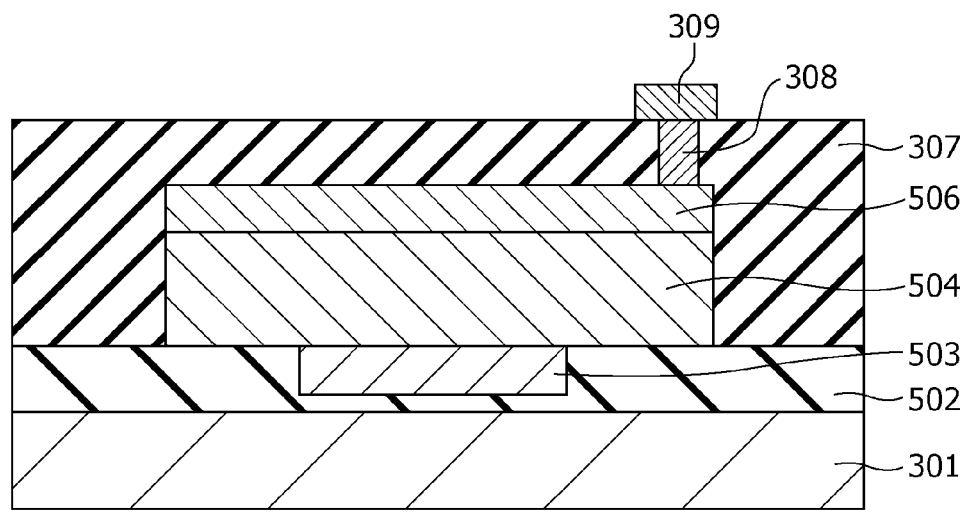

Then, as shown in FIG. 10G, a conductor film 718 is formed on the upper surface of the interlayer insulating film 307 and the inside of the via hole 307b so as to fill the via hole 307b. Then, as shown in FIG. 10H, the conductor film 718 on the interlayer insulating film 307 is removed by CMP to form a via 308 in the via hole 307b. Another conductor film is further formed on the interlayer insulating film 307 and is patterned to form a wiring conductor 309 connected to the via 308.

Figure 10I:
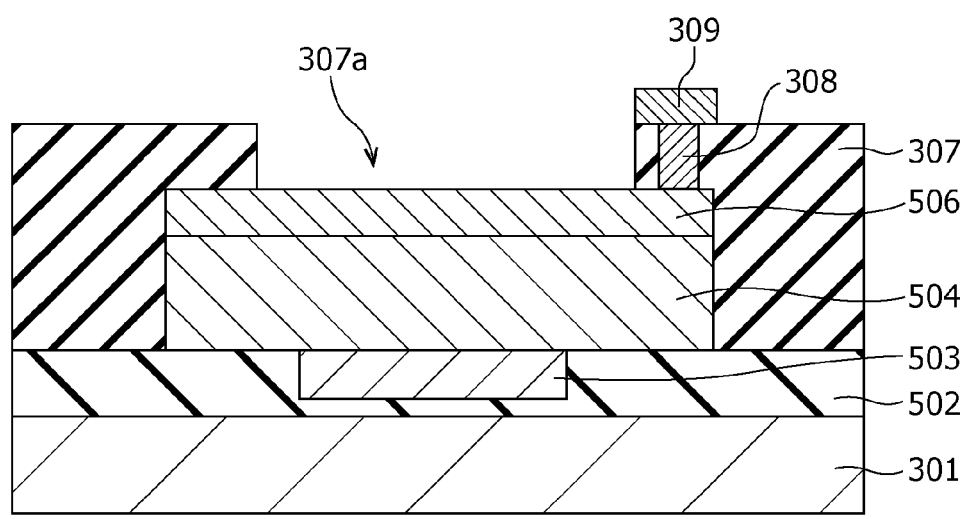

Then, as shown in FIG. 10I, an opening 307a is formed in the interlayer insulating film 307 by etching such that a part of the second electrode 506 is exposed.

Subsequently, a local region 505 is formed in the gas-sensitive resistive film 504 at the portion corresponding to the outline of the first electrode 503 in a planar view by applying an initial break voltage between the first electrode 503 and the second electrode 506. A gas sensor 500 shown in FIG. 9 is thus accomplished.

The resistance change characteristics by voltage application to the thus-configured gas sensor 500 are substantially the same as those by voltage application to the gas sensor 100 shown in FIG. 3. In also the gas sensor 500, the resistance change due to hydrogen-containing gas is caused by the same mechanism as that described for the gas sensor 100. Accordingly, the gas sensor 500 can detect hydrogen-containing gas with a low power consumption.

Modification Example 3

Figure 11:
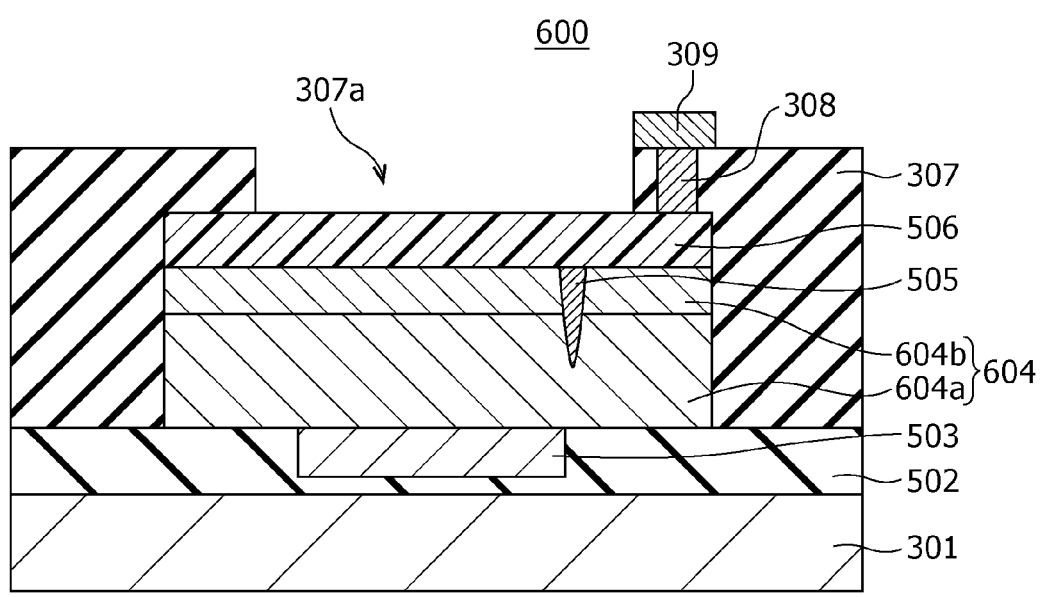
FIG. 11 is a cross-sectional view of a gas sensor according to modification example 3 of Second Embodiment.

FIG. 11 is a cross-sectional view illustrating an exemplary configuration of a gas sensor 600 according to modification example 3 of Second Embodiment. Only the points different from the gas sensor 500 of modification example 2 of Second Embodiment will be described below.

The gas sensor 600 of the modification example differs from the gas sensor 500 of modification example 2 of Second Embodiment in that the gas-sensitive resistive film 604 includes two layers: a first metal oxide layer 604a being in contact with the first electrode 503 and a second metal oxide layer 604b stacked on the first metal oxide layer 604a and being in contact with the second electrode 506. The gas-sensitive resistive film 604 is not limited to of two layers and may include three or more metal oxide layers.

The first metal oxide layer 604a and the second metal oxide layer 604b contain a local region 505 that reversibly changes the degree of oxygen deficiency depending on application of an electric pulse and the presence or absence of hydrogen-containing gas. The local region 505 at least passes through the second metal oxide layer 604b and is in contact with the second electrode 506.

In other words, the gas-sensitive resistive film 604 has a layered structure at least composed of a first metal oxide layer 604a containing a first metal oxide and a second metal oxide layer 604b containing a second metal oxide. The first metal oxide layer 604a is disposed between the first electrode 503 and the second metal oxide layer 604b, and the second metal oxide layer 604b is disposed between the first metal oxide layer 604a and the second electrode 506.

The second metal oxide layer 604b may have a thickness smaller than that of the first metal oxide layer 604a. In such a case, a structure of the local region 505 not being in contact with the first electrode 503 can be easily formed. The metal oxide contained in the second metal oxide layer 604b may have a degree of oxygen deficiency smaller than that of the metal oxide contained in the first metal oxide layer 604a. In this case, since the second metal oxide layer 604b has a resistance value higher than that of the first metal oxide layer 604a, most of the voltage applied to the gas-sensitive resistive film 604 is applied to the second metal oxide layer 604b. This configuration can reduce, for example, the initial break voltage necessary for forming the local region 505.

The gas-sensitive resistive film 604 includes the local region 505 in the vicinity of the interface between the first metal oxide layer 604a and the second metal oxide layer 604b. The degree of oxygen deficiency of the metal oxide contained in the local region 505 is larger than that of the metal oxide contained in the second metal oxide layer 604b and is different from that of the metal oxide contained in the first metal oxide layer 604a.

The local region 505 is formed in the gas-sensitive resistive film 604 by applying an initial break voltage between the first electrode 503 and the second electrode 506. Herein, the initial break voltage is the same as that in First Embodiment, and the description thereof is omitted. The application of the initial break voltage forms a local region 505 that is in contact with the second electrode 506, passes through the second metal oxide layer 604b, partially penetrates into the first metal oxide layer 604a, and is not in contact with the first electrode 503.

The thus-configured gas sensor 600 can generate heat by only the current for detecting the resistance state and can detect hydrogen-containing gas without heating with a separate heater.

(Third Embodiment)

A fuel-cell vehicle according to Third Embodiment includes any one of the gas sensors described in First and Second Embodiments and modification examples thereof and detects hydrogen gas in the vehicle with the gas sensor.

Figure 12:
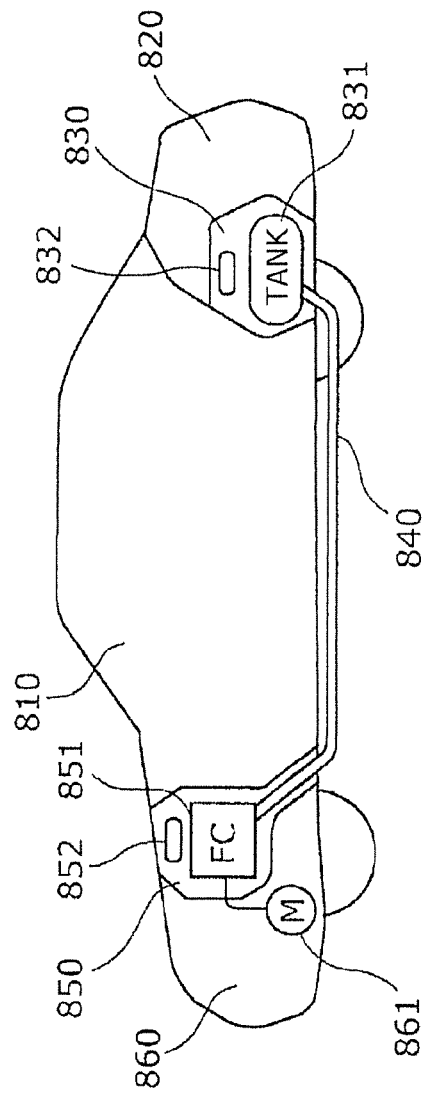
FIG. 12 is a side view of a fuel-cell vehicle according to Third Embodiment.

FIG. 12 is a side view illustrating an exemplary configuration of the fuel-cell vehicle 800 according to Third Embodiment.

The fuel-cell vehicle 800 includes a passenger compartment 810, a trunk 820, a gas tank chamber 830, a fuel tank 831, a gas sensor 832, a pipe 840, a fuel cell chamber 850, a fuel cell 851, a gas sensor 852, a motor chamber 860, and a motor 861.

The fuel tank 831 is disposed in the gas tank chamber 830 and maintains hydrogen gas as the fuel gas. The gas sensor 832 detects fuel gas leakage in the gas tank chamber 830.

The fuel cell 851 includes a fuel cell stack composed of a plurality of stacked cells that are base units each including a fuel electrode, an air electrode, and an electrolyte. The fuel cell 851 is disposed in the fuel cell chamber 850. The hydrogen gas in the fuel tank 831 is sent into the fuel cell 851 in the fuel cell chamber 850 through the pipe 840. Electric power is generated by reacting this hydrogen gas with oxygen gas in the atmosphere in the fuel cell 851. The gas sensor 852 detects hydrogen gas leakage in the fuel cell chamber 850.

The motor 861 is disposed in the motor chamber 860. The electric power generated by the fuel cell 851 rotates the motor 861 and thereby allows the fuel-cell vehicle 800 to travel.

As described above, the gas sensor according to the present disclosure can detect hydrogen-containing gas with a very low power consumption of about 0.01 mW for example. Accordingly, the gas sensor can constantly monitor hydrogen gas leakage by utilizing the excellent power-saving properties, without significantly increasing the stand-by power of the fuel-cell vehicle.

For example, whether hydrogen gas is present or not in the outside of the tank 831 in the gas tank chamber 830 or in the outside of the fuel cell 851 in the fuel cell chamber 850 may be judged based on the quantity of current flowing in the gas sensor 832 or 852 by constantly applying a certain voltage to the gas sensors 832 and 852, regardless of the operation state of the ignition key of the fuel-cell vehicle 800.

Accordingly, since the presence or absence of hydrogen gas leakage has been already judged at, for example, the time of operating the ignition key, the start-up of the fuel-cell vehicle can be shortened, compared with the case of operating the gas sensor for judging the presence or absence of hydrogen gas leakage after operation of the ignition key. In addition, the safety can be improved by continuously monitoring hydrogen gas leakage after running the fuel-cell vehicle, for example, even after the fuel-cell vehicle has been housed in a garage.

The gas sensor, the method of detecting hydrogen gas, and the fuel-cell vehicle according to some aspects of the present disclosure have been described above based on embodiments, but the present disclosure is not limited to these embodiments. Numerous modifications of the embodiments that can be conceived by those skilled in the art and configurations constructed by combining components in the embodiments will fall within the scope of the present disclosure within a range that does not depart from the gist of the present disclosure.

For example, the gas sensor described above may further include a measurement circuit for measuring the current flowing in the gas-sensitive resistive film by applying a certain voltage between the first electrode and the second electrode. Alternatively, the gas sensor may further include a power supply circuit for constantly applying a certain voltage between the first electrode and the second electrode.

Such configurations can provide gas sensors having high convenience as modular components including a measurement circuit or a power supply circuit.

What is claimed is:
1. A gas sensor comprising:
 a first electrode having a first main surface and a second main surface opposite to the first main surface;
 a second electrode having a third main surface facing the second main surface of the first electrode and a fourth main surface opposite to the third main surface;
 a metal oxide layer comprising only a single layer of metal oxide disposed between the first electrode and the second electrode, and being in contact with the second main surface of the first electrode and the third main surface of the second electrode;
an insulating film covering at least a part of the first electrode, a part of the second electrode, and at least a part of the metal oxide layer, wherein:
at least a part of the fourth main surface of the second electrode is not covered with the insulating film and is exposed to gas which contains a gas molecule including a hydrogen atom; and
the metal oxide layer includes a local region being in contact with the second electrode and has a resistance value that decreases with changing oxygen deficiency level in the local region when the second electrode is in contact with the gas molecule; and
a via passing through the insulating film in a portion covering the part of the second electrode and in direct physical contact with the second electrode,
wherein a degree of oxygen deficiency of a metal oxide contained in the local region is larger than a degree of oxygen deficiency of a metal oxide contained in a portion other than the local region in the metal oxide layer.

2. The gas sensor according to claim 1, wherein
the second electrode contains a material having a catalytic action of releasing the hydrogen atom from the gas molecule.

3. The gas sensor according to claim 1, wherein
the second electrode contains at least one selected from the group consisting of platinum, palladium, and an alloy of platinum and palladium.

4. The gas sensor according to claim 1, wherein
the first metal oxide is a transition metal oxide or aluminum oxide.

5. The gas sensor according to claim 4, wherein
the transition metal oxide is one selected from the group consisting of tantalum oxide, hafnium oxide, and zirconium oxide.

6. The gas sensor according to claim 1, wherein
the metal oxide layer is a layer having a property of reversibly transiting between a high resistance state and a low resistance state showing a lower resistance value than the high resistance state based on a voltage applied between the first electrode and the second electrode.

7. The gas sensor according to claim 1, wherein
an area of the metal oxide layer being in contact with the second main surface of the first electrode is smaller than an area of the metal oxide layer being in contact with the third main surface of the second electrode.

8. The gas sensor according to claim 1 further comprising:
a measurement circuit that, in operation, measures current flowing in the metal oxide layer when a voltage is applied between the first electrode and the second electrode.

9. The gas sensor according to claim 1 further comprising:
a power supply circuit that, in operation, applies a voltage between the first electrode and the second electrode.

10. The gas sensor according to claim 1, wherein the local region generates heat by current flowing between the first electrode and the second electrode to reduce the resistance value of the metal oxide layer.

11. The gas sensor according to claim 1 further comprising:
a conductor connected to the via.

12. The gas sensor according to claim 11, wherein
the via is disposed at a position not directly above the first electrode.

13. A fuel-cell vehicle comprising:
a passenger compartment;
a gas tank chamber accommodating a hydrogen gas tank;
a fuel cell chamber accommodating a fuel cell; and
a gas sensor comprising:
a first electrode having a first main surface and a second main surface opposite to the first main surface;
a second electrode having a third main surface facing the second main surface of the first electrode and a fourth main surface opposite to the third main surface;
a metal oxide layer comprising only a single layer of metal oxide disposed between the first electrode and the second electrode, and being in contact with the second main surface of the first electrode and the third main surface of the second electrode; and
an insulating film covering at least a part of the first electrode, a part of the second electrode, and at least a part of the metal oxide layer, wherein:
at least a part of the fourth main surface of the second electrode is not covered with the insulating film and is exposed to gas which contains a gas molecule including a hydrogen atom;
the metal oxide layer includes a local region being in contact with the second electrode and has a resistance value that decreases with changing oxygen deficiency level in the local region when the second electrode is in contact with the gas molecule; and
the gas sensor is disposed in at least one selected from the group consisting of the gas tank chamber and the fuel cell chamber; and
a via passing through the insulating film in a portion covering the part of the second electrode and in direct physical contact with the second electrode,
wherein a degree of oxygen deficiency of a metal oxide contained in the local region is larger than a degree of oxygen deficiency of a metal oxide contained in a portion other than the local region in the metal oxide layer.

* * * * *